(12) United States Patent
Konno et al.

(10) Patent No.: US 10,605,591 B2
(45) Date of Patent: Mar. 31, 2020

(54) SHAPE MEASUREMENT APPARATUS AND SHAPE MEASUREMENT METHOD

(71) Applicant: NIPPON STEEL & SUMITOMO METAL CORPORATION, Tokyo (JP)

(72) Inventors: Yusuke Konno, Tokyo (JP); Takamichi Kobayashi, Tokyo (JP); Toshio Akagi, Tokyo (JP); Atsuhiro Hibi, Tokyo (JP); Nobuhiro Furuya, Tokyo (JP); Akihito Nakazaki, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 0 days.

(21) Appl. No.: 15/738,499

(22) PCT Filed: May 19, 2017

(86) PCT No.: PCT/JP2017/018897
§ 371 (c)(1),
(2) Date: Dec. 20, 2017

(87) PCT Pub. No.: WO2017/204119
PCT Pub. Date: Nov. 30, 2017

(65) Prior Publication Data
US 2018/0180405 A1    Jun. 28, 2018

(30) Foreign Application Priority Data

May 23, 2016 (JP) ................. 2016-102330

(51) Int. Cl.
*G01B 11/24* (2006.01)
*G01N 21/892* (2006.01)
(Continued)

(52) U.S. Cl.
CPC .............. *G01B 11/24* (2013.01); *G01B 11/26* (2013.01); *G01B 11/303* (2013.01);
(Continued)

(58) Field of Classification Search
CPC ....... G01B 11/24; G01B 11/26; G01B 11/303; G01B 11/306; G01N 21/8901;
(Continued)

(56) References Cited

U.S. PATENT DOCUMENTS

| | | | | |
|---|---|---|---|---|
| 3,198,951 A | * | 8/1965 | Lentze | ............... G01N 21/8901 250/208.4 |
| 2003/0044714 A1 | * | 3/2003 | Teraoka | .................. B41C 1/10 430/138 |

(Continued)

FOREIGN PATENT DOCUMENTS

| | | |
|---|---|---|
| JP | 62-62205 A | 3/1987 |
| JP | 5-99639 A | 4/1993 |

(Continued)

OTHER PUBLICATIONS

Espacenet English translation of JP2014153149.*

(Continued)

*Primary Examiner* — Mohamed K Amara
(74) *Attorney, Agent, or Firm* — Birch, Stewart, Kolasch & Birch, LLP

(57) ABSTRACT

A shape measurement apparatus includes: a linear light source that includes a superluminescent diode and applies linear light spreading in a width direction of the strip-shaped body to a surface of the strip-shaped body; a screen on which reflected light of the linear light off the surface of the strip-shaped body is projected; an area camera that captures an image of the reflected light of the linear light projected on the screen; and an arithmetic processing apparatus that calculates the surface shape of the strip-shaped body using the captured image of the reflected light of the linear light captured by the area camera.

16 Claims, 12 Drawing Sheets

(51) Int. Cl.
    *G01B 11/30*     (2006.01)
    *G01B 11/26*     (2006.01)
    *G01N 21/89*     (2006.01)

(52) U.S. Cl.
    CPC ....... *G01B 11/306* (2013.01); *G01N 21/8901* (2013.01); *G01N 21/892* (2013.01); *G01N 2021/8908* (2013.01); *G01N 2021/8918* (2013.01); *G01N 2201/062* (2013.01)

(58) Field of Classification Search
    CPC ........... G01N 21/892; G01N 2201/062; G01N 2021/8908; G01N 2021/8918
    See application file for complete search history.

(56) References Cited

U.S. PATENT DOCUMENTS

| | | | | |
|---|---|---|---|---|
| 2004/0000859 | A1* | 1/2004 | Ito | H01J 9/263 |
| | | | | 313/477 R |
| 2007/0246158 | A1* | 10/2007 | Yamazaki | H05K 3/325 |
| | | | | 156/306.6 |
| 2009/0130434 | A1* | 5/2009 | Zhu | C04B 35/58014 |
| | | | | 428/328 |
| 2010/0039708 | A1* | 2/2010 | Suzuki | G02B 1/11 |
| | | | | 359/601 |
| 2012/0008206 | A1* | 1/2012 | Haga | G02B 5/0221 |
| | | | | 359/488.01 |
| 2012/0076923 | A1* | 3/2012 | Bucher | G01B 11/0608 |
| | | | | 427/9 |
| 2012/0321348 | A1* | 12/2012 | Toriu | G03G 15/751 |
| | | | | 399/159 |
| 2013/0030270 | A1* | 1/2013 | Chiou | A61B 5/0476 |
| | | | | 600/344 |
| 2014/0168368 | A1 | 6/2014 | Doucet et al. | |
| 2015/0321498 | A1* | 11/2015 | Toyota | B42D 5/003 |
| | | | | 428/143 |
| 2016/0169798 | A1 | 6/2016 | Kostka et al. | |
| 2016/0249541 | A1* | 9/2016 | Nishimura | A01G 24/00 |
| | | | | 47/59 S |
| 2016/0357294 | A1* | 12/2016 | Ozeki | C03C 15/00 |
| 2017/0038703 | A1* | 2/2017 | Horiuchi | G03G 15/043 |
| 2017/0085014 | A1* | 3/2017 | Nishida | C25D 5/12 |
| 2017/0131513 | A1* | 5/2017 | Lin | G02B 7/021 |
| 2017/0227876 | A1* | 8/2017 | Morooka | G03G 9/1132 |
| 2017/0242354 | A1* | 8/2017 | Saito | G03G 9/08 |
| 2018/0071881 | A1* | 3/2018 | Horie | B24B 29/00 |
| 2018/0119359 | A1* | 5/2018 | Gorden | D21H 19/74 |
| 2019/0301853 | A1* | 10/2019 | Klose | G01N 21/952 |

FOREIGN PATENT DOCUMENTS

| | | |
|---|---|---|
| JP | 8-233541 A | 9/1996 |
| JP | 11-316111 A | 11/1999 |
| JP | 2004-184397 A | 7/2004 |
| JP | 2009-111230 A | 5/2009 |
| JP | 2012-78144 A | 4/2012 |
| JP | 2014-153149 A | 8/2014 |
| JP | 2014-178323 A | 9/2014 |
| WO | WO 2007/032216 A1 | 3/2007 |

OTHER PUBLICATIONS

GoogleEnglish translation of JP2004184397.*
https://www.innolume.com/products/SLD.htm.*
Extended European Search Report dated Jun. 20, 2018, in European Patent Application No. 17802711.6.
Paschotta, R., "Superluminescent diodes," Encyclopedia of Laser Physics and Technology (Oct. 1, 2008), pp. 1-3.
Korean Office Action dated Nov. 27, 2018, for corresponding Korean Application No. 10-2018-7002605, with partial English translation.
Beckmann, "Scattering by Composite Rough Surfaces", Proceedings of the IEEE, 1965, vol. 53, No. 8, pp. 1012-1015.
International Search Report for PCT/JP2017/018897 dated Jul. 4, 2017.
Office Action for JP 2017-550258 dated Nov. 28, 2017.
Written Opinion of the International Searching Authority for PCT/JP2017/018897 (PCT/ISA/237) dated Jul. 4, 2017.

* cited by examiner

FIG. 6
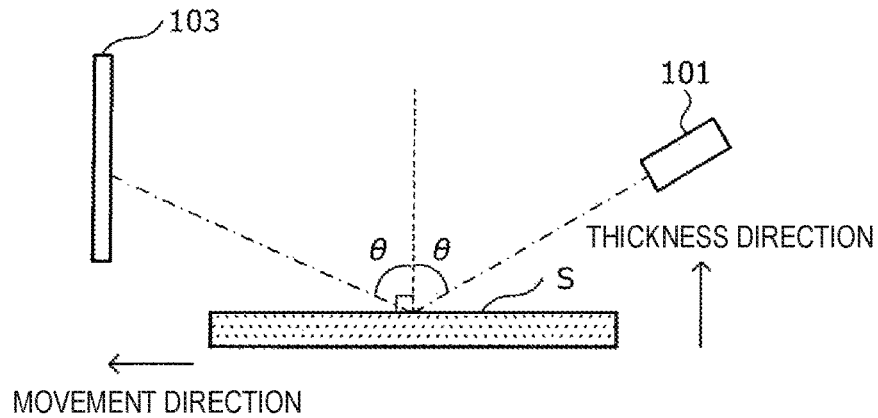
FIG. 7
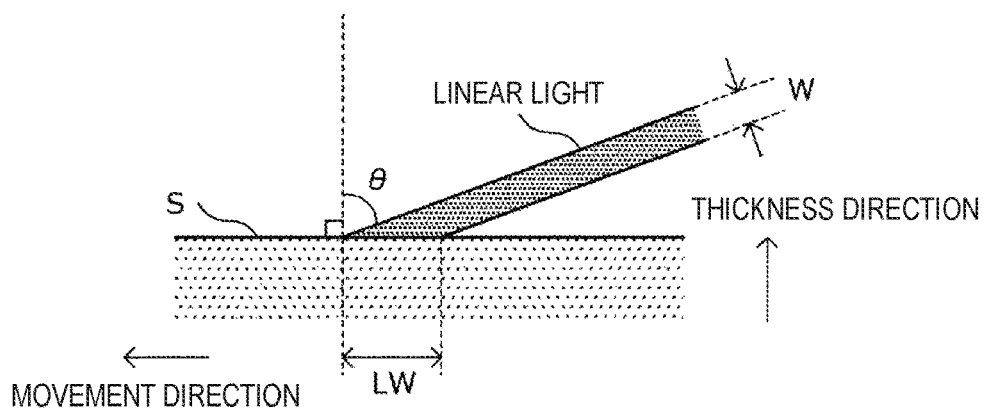
FIG. 8
| SIZE OF UNEVENNESS FORMED ON STEEL PLATE SURFACE | | 2 mm |
|---|---|---|
| DETECTABILITY | ANGLE OF INCIDENCE 87 DEGREES (LINE WIDTH 1.3mm) | OK |
| | ANGLE OF INCIDENCE 88 DEGREES (LINE WIDTH 2.0mm) | OK |
| | ANGLE OF INCIDENCE 89 DEGREES (LINE WIDTH 4.0mm) | NG |

SHAPE MEASUREMENT APPARATUS AND SHAPE MEASUREMENT METHOD

TECHNICAL FIELD

The present invention relates to a shape measurement apparatus and a shape measurement method.

BACKGROUND ART

One of methods for measuring the surface shape of a measurement object is to use illumination light utilizing laser light or the like, and capture an image of reflected light from the measurement object of the illumination light to measure the surface shape of the measurement object.

For example, Patent Literature 1 below discloses a technology of, using a moving strip-shaped body (e.g., a steel sheet) as a measurement object, measuring a surface shape of the strip-shaped body on the basis of the principle of an optical lever. Specifically, in Patent Literature 1, linear light applied along the width direction of the strip-shaped body is specularly reflected to be projected on a screen, and a reflected image on the screen is captured by an area camera; thus, a stripe image is obtained. After that, the surface shape of the strip-shaped body is measured by performing predetermined image processing on the obtained stripe image.

In addition, as a technology similar to Patent Literature 1, though it is not a technology based on the principle of an optical lever as disclosed in Patent Literature 1, Patent Literature 2 below discloses a technology of applying light beams of laser light to the surface of a planar object to be inspected, projecting, on a screen, reflected light of the light beams off the surface of the planar object to be inspected, and then observing light and dark on the screen caused by sparseness and denseness of the light beams due to unevenness of the surface of the planar object to be inspected.

CITATION LIST

Patent Literature

Patent Literature 1: JP 2004-184397A
Patent Literature 2: JP H5-99639A

Non-Patent Literature

Non-Patent Literature 1: P. Beckmann, "Scattering by composite rough surfaces", Proceedings of the IEEE, vol. 53, issue. 8, 1965, P. 1012-1015.

SUMMARY OF INVENTION

Technical Problem

Patent Literature 1 describes that a laser light source is mainly used as a light source of the linear light. However, as a result of studies, the present inventors have found that in the case where laser light is used as the linear light, speckle noise occurs in the reflected image of the linear light projected on the screen, which makes measurement with high precision difficult. In addition, Patent Literature 1 discloses, as light sources other than a laser light source, a white light source, a combination of a strip-shaped optical fiber bundle and a rod lens, and a combination of a straight-tube fluorescent lamp, a slit, and a cylindrical lens. However, it has been found that in the case where these light sources are used, it is difficult to focus light into thin linear light because a light-emitting part is large, which makes measurement with high precision difficult.

In Patent Literature 2, a light beam of laser light is applied to have a spread angle without being focused on the surface of the planar object to be inspected; thus, an image of reflected light on the screen is large. A large image on the screen results in a large data reading area in a camera, and a restriction in image transfer speed makes it difficult to perform high-speed flaw search. In addition, also in Patent Literature 2, since a laser light source is used as a light source, speckle noise occurs in the reflected image of the linear light projected on the screen. In Patent Literature 2, to remove the speckle noise, (a) the resolution of the camera is made lower than the average size of speckle noise, and then (b) a decrease in detection sensitivity due to the decrease in camera resolution is prevented by increasing a distance between the screen and a reflection position on the object to be inspected. However, if the distance between the screen and the reflection position is increased, spread of reflected light makes an image of the reflected light on the screen dark, and longer exposure time is needed. Therefore, in the technology disclosed in Patent Literature 2, it is difficult to perform high-speed flaw search.

Furthermore, in the technology disclosed in Patent Literature 2, a change in reflectance on the surface of the planar object to be inspected cannot be separated from a change in shape of the surface of the planar object to be inspected, as mentioned in the literature. Therefore, when the technology disclosed in Patent Literature 2 is applied to a metallic body typified by steel products, for example, there is a high possibility that harmless dirt is misdetected as a change in surface shape in the case where harmless dirt or the like in a production line is attached to the surface.

Hence, the present invention is made in view of the above problems, and an object of the present invention is to provide a shape measurement apparatus and a shape measurement method that are capable of measuring a surface shape of a strip-shaped body made of a metallic body at higher speed with higher precision while suppressing occurrence of speckle noise.

Solution to Problem

According to an aspect of the present invention in order to achieve the above-mentioned object, there is provided a shape measurement apparatus configured to measure a surface shape of a strip-shaped body made of a metallic body, the shape measurement apparatus including: a linear light source that includes a superluminescent diode and applies linear light spreading in a width direction of the strip-shaped body to a surface of the strip-shaped body; a screen on which reflected light of the linear light off the surface of the strip-shaped body is projected; an area camera that captures an image of the reflected light of the linear light projected on the screen; and an arithmetic processing apparatus that calculates the surface shape of the strip-shaped body using the captured image of the reflected light of the linear light captured by the area camera. The linear light source has a spectral half-width of 20 nm or more, and is placed in a manner that an angle $\theta$ formed by an optical axis of the linear light source and a direction normal to the surface of the strip-shaped body and a wavelength of the linear light satisfy Formula (I) below related to specularity of the strip-shaped body.

[Math. 1]

$$\frac{\cos\theta}{\lambda} \leq \frac{1}{2\pi} \qquad \text{Formula (I)}$$

On the surface of the strip-shaped body, a line width W of the linear light along a longitudinal direction of the strip-shaped body is preferably controlled so as to satisfy Formula (II) below, where $L_{min}$ is a minimum value of a size of the surface shape to be measured along the longitudinal direction, and $\lambda$ is the wavelength of the linear light.

[Math. 2]

$$\frac{W}{L_{min}} \leq \frac{\lambda}{2\pi} \qquad \text{Formula (II)}$$

The wavelength of the linear light is preferably equal to or greater than 800 nm and equal to or less than 1700 nm.

The linear light source is preferably placed on the basis of the Formula (I) in a manner that the angle $\theta$ formed by the optical axis of the linear light source and the direction normal to the surface of the strip-shaped body falls within a range of equal to or greater than 74 degrees and equal to or less than 88 degrees.

Power density of the linear light on the surface of the strip-shaped body is preferably 55 mW/cm² or more.

In regard to surface roughness of a projection plane of the reflected light of the linear light on the screen, it is preferable that a mean width RSm of roughness profile elements prescribed in JIS B0601:2001 be 10 times or more greater than the wavelength of the linear light, and be 1/10 or less of a line width of the reflected light of the linear light along a height direction of the screen on the screen.

The linear light may be applied to the surface of the strip-shaped body positioned on a surface of a roll having a predetermined curvature.

The arithmetic processing apparatus may calculate an inclination angle of the surface of the strip-shaped body as information on the surface shape, on the basis of an amount of displacement of the reflected light from a reference position in the captured image.

The arithmetic processing apparatus may calculate a height of the surface of the strip-shaped body as information on the surface shape, by integrating a tangent of the calculated inclination angle of the surface of the strip-shaped body along a relative movement direction of the area camera and the strip-shaped body.

The arithmetic processing apparatus may inspect a shape of the strip-shaped body by comparing the calculated inclination angle of the surface of the strip-shaped body with a predetermined threshold value.

According to another aspect of the present invention in order to achieve the above-mentioned object, there is provided a shape measurement method configured to measure a surface shape of a strip-shaped body made of a metallic body, the shape measurement method including: an irradiation step of applying linear light spreading in a width direction of the strip-shaped body to a surface of the strip-shaped body, using a linear light source that includes a superluminescent diode; a step of projecting, on a screen, reflected light of the linear light off the surface of the strip-shaped body; an image capturing step of capturing an image of the reflected light of the linear light projected on the screen, using an area camera; and a calculation step of calculating the surface shape of the strip-shaped body using the captured image of the reflected light of the linear light captured by the area camera. The linear light source has a spectral half-width of 20 nm or more, and is placed in a manner that an angle $\theta$ formed by an optical axis of the linear light source and a direction normal to the surface of the strip-shaped body and a wavelength $\lambda$ of the linear light satisfy Formula (I) below related to specularity of the strip-shaped body.

[Math. 3]

$$\frac{\cos\theta}{\lambda} \leq \frac{1}{2\pi} \qquad \text{Formula (I)}$$

On the surface of the strip-shaped body, a line width W of the linear light along a longitudinal direction of the strip-shaped body is preferably controlled so as to satisfy Formula (II) below, where $L_{min}$ is a minimum value of a size of the surface shape to be measured along the longitudinal direction, and $\lambda$ is the wavelength of the linear light.

[Math. 4]

$$\frac{W}{L_{min}} \leq \frac{\lambda}{2\pi} \qquad \text{Formula (II)}$$

The wavelength of the linear light is preferably equal to or greater than 800 nm and equal to or less than 1700 nm.

The linear light source is preferably placed on the basis of the Formula (I) in a manner that the angle $\theta$ formed by the optical axis of the linear light source and the direction normal to the surface of the strip-shaped body falls within a range of equal to or greater than 74 degrees and equal to or less than 88 degrees.

Power density of the linear light on the surface of the strip-shaped body is preferably 55 mW/cm² or more.

In regard to surface roughness of a projection plane of the reflected light of the linear light on the screen, it is preferable that a mean width RSm of roughness profile elements prescribed in JIS B0601:2001 be 10 times or more greater than the wavelength of the linear light, and be 1/10 or less of a line width of the reflected light of the linear light along a height direction of the screen on the screen.

The linear light may be applied to the surface of the strip-shaped body positioned on a surface of a roll having a predetermined curvature.

The calculation step may calculate an inclination angle of the surface of the strip-shaped body as information on the surface shape, on the basis of an amount of displacement of the reflected light from a reference position in the captured image.

The calculation step may calculate a height of the surface of the strip-shaped body as information on the surface shape, by integrating a tangent of the calculated inclination angle of the surface of the strip-shaped body along a relative movement direction of the area camera and the strip-shaped body.

The shape measurement method may further include an inspection step of inspecting a shape of the strip-shaped body by comparing the calculated inclination angle of the surface of the strip-shaped body with a predetermined threshold value.

Advantageous Effects of Invention

As described above, according to the present invention, a surface shape of a strip-shaped body made of a metallic body can be measured at higher speed with higher precision while occurrence of speckle noise is suppressed.

BRIEF DESCRIPTION OF DRAWINGS

FIG. 6 is an explanatory diagram for a strip-shaped body image capturing apparatus according to the embodiment.

FIG. 7 is an explanatory diagram for a strip-shaped body image capturing apparatus according to the embodiment.

FIG. 8 is an explanatory diagram illustrating the relationship between an angle of incidence of linear light and a detection situation of a surface shape.

DESCRIPTION OF EMBODIMENTS

Figure 1:
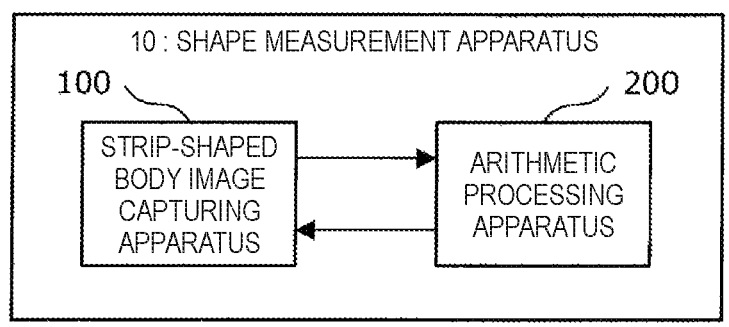
FIG. 1 is an explanatory diagram schematically illustrating an overall configuration of a shape measurement apparatus according to an embodiment of the present invention.

Hereinafter, (a) preferred embodiment(s) of the present invention will be described in detail with reference to the appended drawings. In this specification and the appended drawings, structural elements that have substantially the same function and structure are denoted with the same reference numerals, and repeated explanation of these structural elements is omitted.

(Overall Configuration of Shape Measurement Apparatus)

First, an overall configuration of a shape measurement apparatus according to an embodiment of the present invention will be described with reference to FIG. 1. FIG. 1 is an explanatory diagram schematically illustrating an overall configuration of a shape measurement apparatus according to the present embodiment.

A shape measurement apparatus 10 according to the present embodiment is an apparatus that measures a surface shape of a strip-shaped body made of a metallic body, and measures the surface shape of the strip-shaped body on the basis of the principle of an optical lever. As illustrated in FIG. 1, the shape measurement apparatus 10 according to the present embodiment mainly includes a strip-shaped body image capturing apparatus 100 and an arithmetic processing apparatus 200.

Here, a strip-shaped body to be used as a measurement object of the shape measurement apparatus 10 according to the present embodiment is not particularly limited as long as its surface reflects illumination light. In the shape measurement apparatus 10 according to the present embodiment, a strip-shaped body to be used as a measurement object is, for example, a metallic body, such as various steel sheets including a plated steel sheet and various alloy steel sheets, and various nonferrous metal sheets.

The strip-shaped body image capturing apparatus 100 mainly includes a linear light source 101, a screen 103, and an area camera 105, which are described later.

Under control of the arithmetic processing apparatus 200 described later, the strip-shaped body image capturing apparatus 100 applies, using the linear light source 101, linear light to the surface of a strip-shaped body that moves by being conveyed on a predetermined conveyor line. In addition, under control of the arithmetic processing apparatus 200 described later, the strip-shaped body image capturing apparatus 100 sequentially captures, using the area camera 105, images of reflected light of the linear light off the surface of the strip-shaped body that is projected on the screen 103, and outputs a plurality of captured images obtained as a result of the image capturing to the arithmetic processing apparatus 200.

The conveyor line that conveys the strip-shaped body serving as a measurement object is provided with a pulse logic generator (PLG) or the like, and a PLG signal of one pulse is output to the arithmetic processing apparatus 200 at regular intervals (e.g., each time the strip-shaped body is moved x mm by the conveyor line). Each time when acquiring a control signal output in accordance with the PLG signal from the arithmetic processing apparatus 200, the strip-shaped body image capturing apparatus 100 captures, using the area camera 105, an image of reflected light of the linear light off the surface of the strip-shaped body that is projected on the screen 103. A detailed configuration of this strip-shaped body image capturing apparatus 100 will be described later.

The arithmetic processing apparatus 200 controls application of linear light by the linear light source 101 and an image capturing process of reflected light of the linear light by the area camera 105. In addition, the arithmetic processing apparatus 200 calculates a surface shape of the strip-shaped body by performing predetermined image processing described in detail later on a plurality of captured images of the reflected light of the linear light that are captured by the strip-shaped body image capturing apparatus 100. A detailed configuration of this arithmetic processing apparatus 200 also will be described later.

The strip-shaped body image capturing apparatus 100 and the arithmetic processing apparatus 200 function in a coordinated fashion; thus, the shape measurement apparatus 10 according to the present embodiment measures a surface shape of a moving strip-shaped body at higher speed in real time.

(Configuration of Strip-Shaped Body Image Capturing Apparatus 100)

Next, detailed description will be given on a configuration of the strip-shaped body image capturing apparatus 100 included in the shape measurement apparatus 10 according to the present embodiment, with reference to FIGS. 2 to 10.

Figure 2:
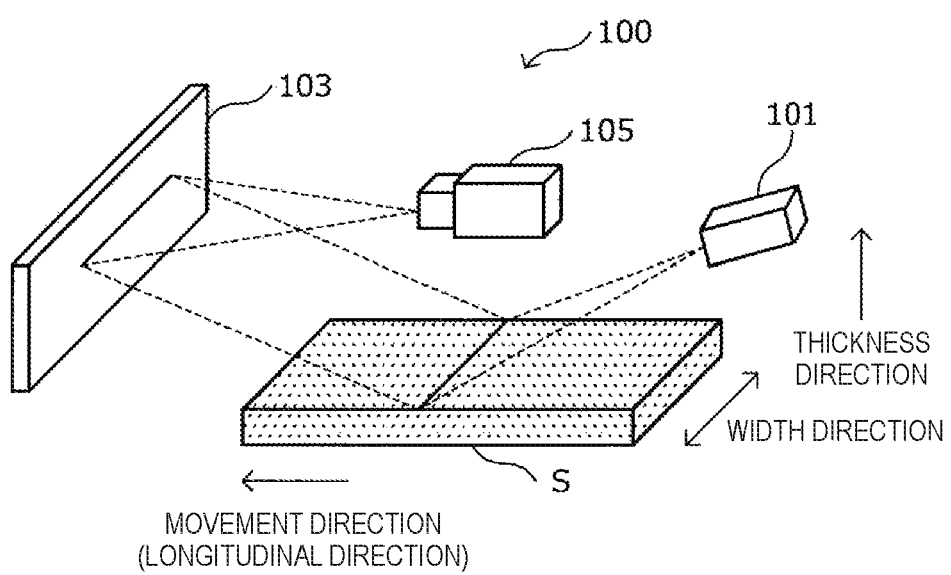
FIG. 2 is an explanatory diagram schematically illustrating an example of a configuration of a strip-shaped body image capturing apparatus included in a shape measurement apparatus according to the embodiment.
Figure 3:
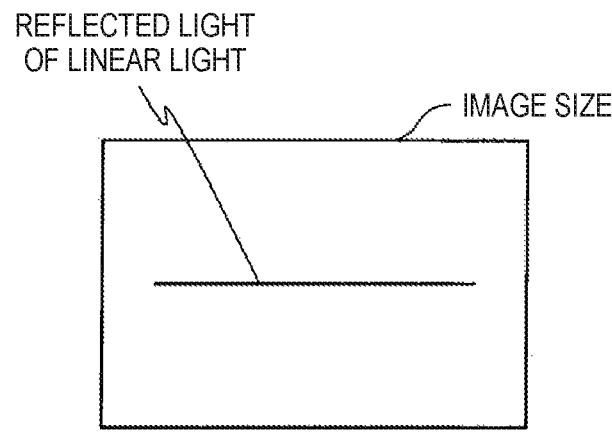
FIG. 3 is an explanatory diagram schematically illustrating an example of a captured image generated by a strip-shaped body image capturing apparatus according to the embodiment.
Figure 9:
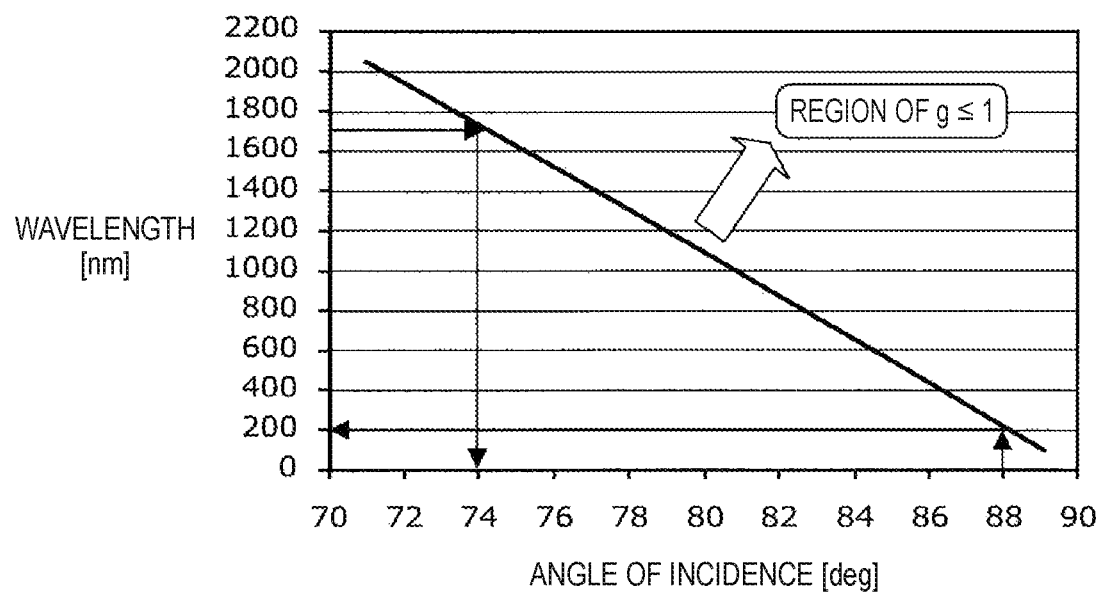
FIG. 9 is a graph showing the relationship between a specular reflection state and a wavelength and an angle of incidence of linear light.
Figure 10:
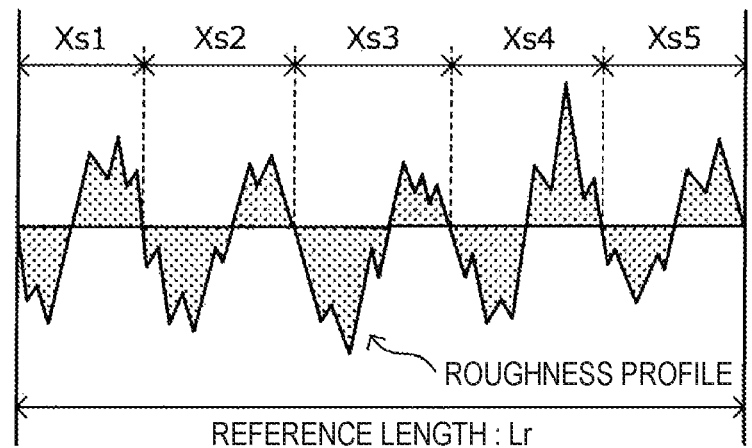
FIG. 10 is an explanatory diagram for a mean width RSm of roughness profile elements.

FIG. 2 is an explanatory diagram schematically illustrating an example of a configuration of a strip-shaped body image capturing apparatus included in a shape measurement apparatus according to the present embodiment. FIG. 3 is an explanatory diagram schematically illustrating an example of a captured image generated by a strip-shaped body image capturing apparatus according to the present embodiment. FIGS. 4A, 4B, 6, and 7 are explanatory diagrams for a strip-shaped body image capturing apparatus according to the present embodiment. FIG. 5 is a graph showing the relationship between a spectral half-width of linear light and speckle noise. FIG. 8 is an explanatory diagram illustrating the relationship between an angle of incidence of linear light and a detection situation of a surface shape. FIG. 9 is a graph showing the relationship between a specular reflection state and a wavelength and an angle of incidence of linear light. FIG. 10 is an explanatory diagram for a mean width RSm of roughness profile elements.

<Overall Configuration of Strip-Shaped Body Image Capturing Apparatus 100>

The strip-shaped body image capturing apparatus 100 mainly includes the linear light source 101, the screen 103, and the area camera 105, which are described later.

The strip-shaped body image capturing apparatus 100 uses the linear light source 101 to apply, to the surface of a moving strip-shaped body S, linear light, which is light that spreads along the width direction of the strip-shaped body and has a narrow width in the movement direction, and projects reflected light of the linear light off the surface of the strip-shaped body S on the screen 103. Then, the area camera 105 is used to capture a plurality of images of the reflected light of the linear light projected on the screen 103.

It may be possible to configure the linear light source 101 with a known light source, such as various lasers and a light emitting diode (LED). In the present embodiment, however, the linear light source 101 is configured with a superluminescent diode (SLD), among these known light sources, in order to effectively prevent speckle noise described later.

The linear light source 101 applies, to the surface of the strip-shaped body S moving in a predetermined direction, linear light, which is light that spreads along the width direction of the strip-shaped body S and has a narrow width in the movement direction. As such a linear light source 101, it is possible to use a combination of the superluminescent diode mentioned above and various lenses such as a rod lens. On the basis of a timing control signal sent from the arithmetic processing apparatus 200, light emitted from the linear light source 101 is spread into a fan-shaped plane while being focused toward the surface of the strip-shaped body S by a lens such as a rod lens. Thus, light with a linear shape (i.e., linear light) that spreads in the width direction is applied from the linear light source 101 to the entire width direction of the surface of the strip-shaped body S. Note that in the linear light source 101 according to the present embodiment, a lens other than a rod lens, such as a cylindrical lens and a Powell lens, can be used as long as it can spread emitted light into a fan shape while focusing the emitted light.

Detailed description will be given later on characteristics of linear light emitted from the linear light source 101, an angle of incidence of linear light on the surface of the strip-shaped body S, and the like.

As schematically illustrated in FIG. 2, the screen 103 is provided at a position facing the linear light source 101, and reflected light of linear light reflected off the surface of the strip-shaped body S is projected on the screen 103. The screen 103 has a breadth that allows projection of reflected light corresponding to the entire width of the strip-shaped body S, in accordance with a spread angle of linear light and a projection distance to the screen. In addition, the height of the screen 103 is set to a height such that reflected light is present on a projection plane of the screen 103 even if a projection position of reflected light changes in accordance with the shape of the strip-shaped body S, vibration accompanying the movement of the strip-shaped body S, a change in thickness of the strip-shaped body S, or the like.

As schematically illustrated in FIG. 2, the area camera 105 is provided at a position facing the screen 103. The area camera 105 is equipped with a lens having a predetermined focal length, and an image sensor, such as a charge coupled device (CCD) or a complementary metal oxide semiconductor (CMOS). The area camera 105 captures an image of reflected light of linear light off the surface of the strip-shaped body S that is projected on the projection plane of the screen 103, each time the strip-shaped body S moves by a predetermined distance, to generate captured images. Here, an angle of view of the area camera 105 is adjusted in advance with reference to operation data in the past, etc. so that the reflected light of the linear light projected on the screen 103 is included in a field of view, and the area camera 105 is set so as to capture images of the projection plane of the screen 103 under the same image capturing conditions. Then, the area camera 105 outputs the generated captured images to the arithmetic processing apparatus 200.

Consequently, a captured image generated by the area camera 105 is an image in which, as schematically illustrated in FIG. 3, reflected light of linear light appears at some position in a full-frame image size.

The area camera 105 is controlled by the arithmetic processing apparatus 200, and a trigger signal for image capturing is output from the arithmetic processing apparatus 200 each time the strip-shaped body S moves by a predetermined distance. In response to the trigger signal output from the arithmetic processing apparatus 200, the area camera 105 sequentially captures images of the surface of the screen 103 on which reflected light of linear light is projected, and outputs the generated plurality of captured images to the arithmetic processing apparatus 200.

Figure 4A:
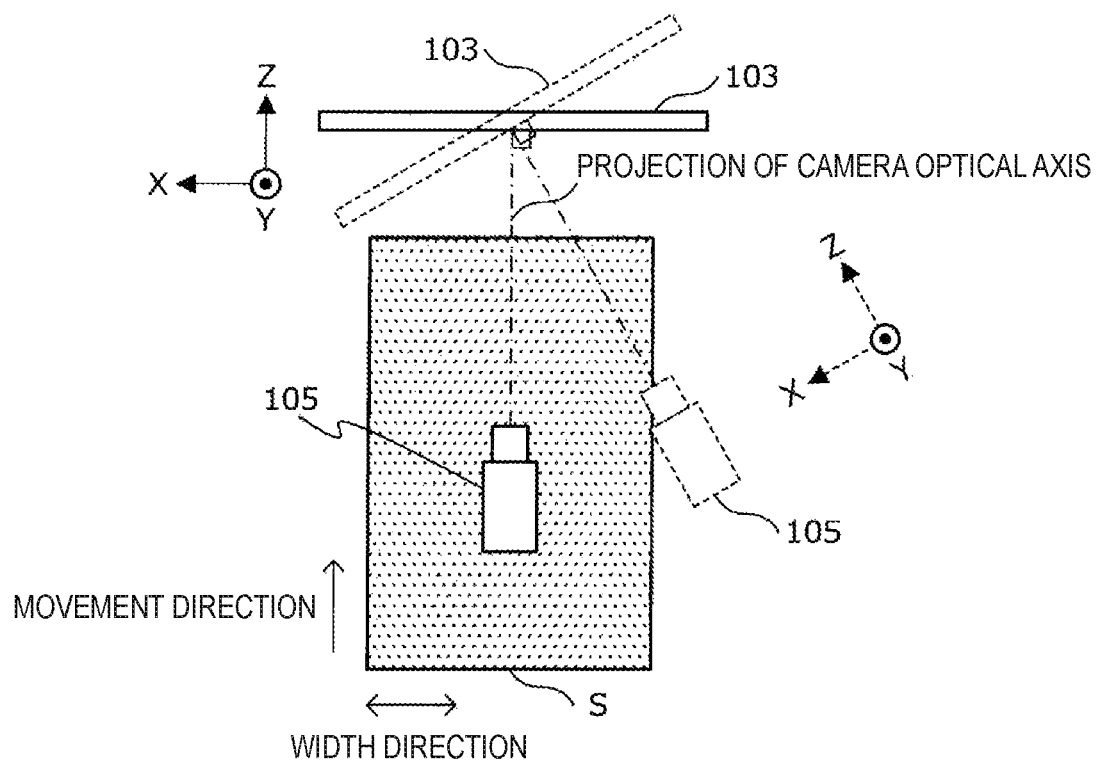
FIG. 4A is an explanatory diagram for a strip-shaped body image capturing apparatus according to the embodiment.
Figure 4B:
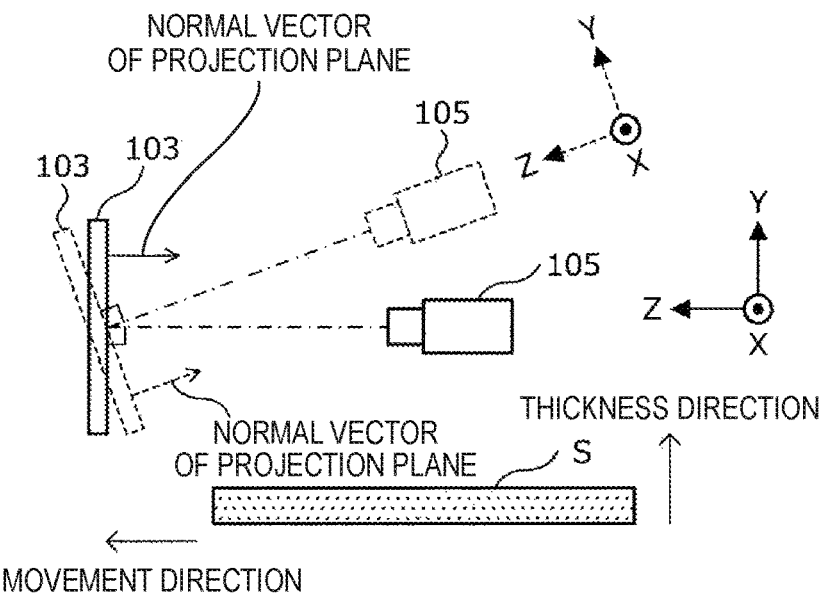
FIG. 4B is an explanatory diagram for a strip-shaped body image capturing apparatus according to the embodiment.
Figure 5:
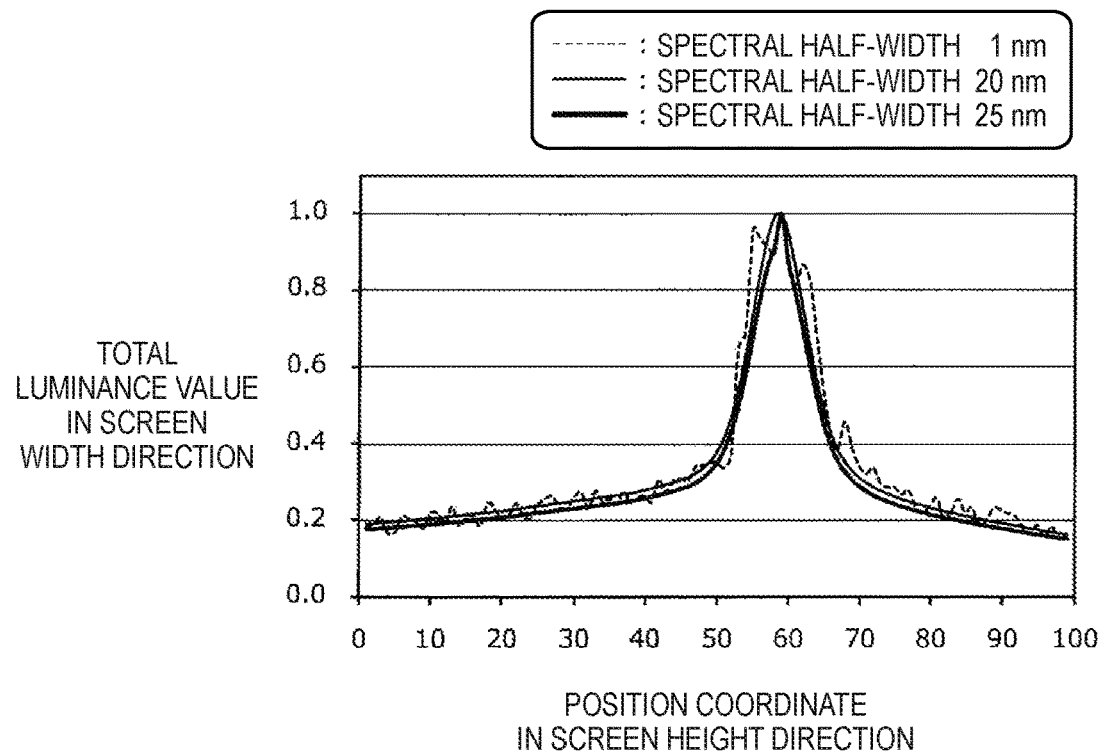
FIG. 5 is a graph showing the relationship between a spectral half-width of linear light and speckle noise.

Here, an X-Y-Z orthogonal coordinate system (right-handed system) fixed to the area camera 105, as illustrated in FIGS. 4A and 4B, is defined. In this coordinate system, the width direction of an image capturing field of view of the area camera 105 is set as an X-axis direction, the height direction of the image capturing field of view of the area camera 105 is set as a Y-axis direction, and an optical-axis direction of the area camera 105 is set as a Z-axis direction.

Now, the positional relationship between the screen 103 and the area camera 105 will be described using FIGS. 4A and 4B.

As illustrated in FIGS. 4A and 4B, the screen 103 is placed in a manner that in the X-Y-Z coordinate system, a normal vector of the projection plane does not have an X component (in other words, the value of the X component is zero). That is, the positional relationship between the screen 103 and the area camera 105 may be a relationship indicated by a solid line in FIG. 4A, or a relationship indicated by a broken line in FIG. 4A. Thus, in the field of view of the area camera 105, an image resolution along the width direction can be made uniform. Moreover, since it is acceptable as long as the image resolution along the width direction is uniform, the positional relationship between the screen 103 and the area camera 105 may be a relationship indicated by a solid line in FIG. 4B, or a relationship indicated by a broken line in FIG. 4B. Furthermore, since the image resolution along the width direction is uniform, in FIG. 4B, one of the screen 103 and the area camera 105 may be positioned at a place indicated by the solid line, and the other may be positioned at a place indicated by the broken line.

Note that although FIG. 2 illustrates a case where only one linear light source 101 is provided, in the strip-shaped body image capturing apparatus 100, a plurality of linear light sources 101 may be provided to apply a plurality of beams of linear light to the surface of the strip-shaped body S. On this occasion, the plurality of beams of linear light are preferably applied to the surface of the strip-shaped body S to be parallel to each other at constant intervals along the movement direction. Moreover, needless to say, in the case where the width direction of the strip-shaped body S is too large with respect to the field of view of the area camera 105, a plurality of area cameras 105 may be provided to capture images of reflected light of linear light in fields of view of the respective area cameras.

<Linear light source 101>

Now, detailed description will be given on the linear light source 101 included in the strip-shaped body image capturing apparatus 100 according to the present embodiment, with reference to FIGS. 5 to 9.

By applying linear light satisfying conditions described in detail later, the linear light source 101 according to the present embodiment can prevent occurrence of speckle noise on the surface of the strip-shaped body S and on the projection plane of the screen 103. Consequently, the strip-shaped body image capturing apparatus 100 according to the present embodiment can capture an image of the surface shape of the strip-shaped body S at higher speed with higher precision, without lengthening exposure time in image capturing.

[Spectral Half-Width]

Lower Limit of Spectral Half-Width

First, attention is focused on a light source spectrum (the relationship between a wavelength and intensity of irradiation light) of linear light applied from the linear light source 101 according to the present embodiment. In the linear light source 101 according to the present embodiment, a superluminescent diode is used as a light source, and a half-width (full width at half maximum) of a spectrum of linear light is set to 20 nm or more. In the linear light source 101 according to the present embodiment, occurrence of speckle noise can be prevented by setting the spectral half-width of linear light to be emitted to 20 nm or more.

A superluminescent diode that emits light of a central wavelength of 800 nm was used as the linear light source 101 illustrated in FIG. 2, and linear light was applied to a flat surface of a steel sheet with a spectral half-width changed, and images of reflected light of linear light projected on the projection plane of the screen 103 were captured. Then, for each of the obtained captured images, the sum of luminance values of the captured image was calculated along the screen width direction at each position in the screen height direction. Here, the spectral half-width was set to three types of values, 20 nm, 25 nm, and 1 nm, which substantially corresponds to a spectral half-width of typical laser light. The obtained result is shown in FIG. 5. Note that in FIG. 5, normalization is performed so that the total luminance value has a maximum value of 1.

It is apparent from FIG. 5 that in the case where the spectral half-width is 20 nm and the case where the spectral half-width is 25 nm, the total luminance value in the screen width direction changes smoothly. On the other hand, in the case where the spectral half-width is 1 nm, the total luminance value in the screen width direction vibrates minutely.

In addition, in the case where the spectral half-width is 20 nm and the case where the spectral half-width is 25 nm, a position coordinate in the screen height direction that gives the maximum total luminance value is a common position of coordinate 60, and the value of the total luminance value smoothly decreases as going away from the position coordinate that gives the maximum total luminance value. On the other hand, in the case where the spectral half-width is 1 nm, the position coordinate that gives the maximum total luminance value is a common position of coordinate 60, but a position coordinate indicating an extremely high total luminance value is present even at a position away from the position coordinate that gives the maximum total luminance value.

The manner of vibration of the total luminance value when the spectral half-width is 1 nm, which is illustrated in FIG. 5, corresponds to speckle noise. This result demonstrates that setting a half-width of a light source spectrum of linear light to 20 nm or more is useful for preventing occurrence of speckle noise.

Also in the case where the wavelength of light applied from a light source was changed from 800 nm, the relationship between a spectral half-width and the total luminance value exhibited a behavior similar to that in FIG. 5.

Upper Limit of Spectral Half-Width

In the case where a half-width of a spectrum of linear light is large, chromatic aberration of an optical system makes it difficult to focus light, and a restriction in a line width on the surface, which is described later, cannot be satisfied. Therefore, an upper limit of a spectral half-width depends on characteristics of the optical system that generates linear light, and a value of a line width to be achieved.

In the strip-shaped body image capturing apparatus 100 according to the present embodiment, for the linear light source 101, a superluminescent diode is used as an incoherent light source capable of emitting a light beam satisfying the spectral half-width described above. Using a superluminescent diode as the linear light source 101 not only enables suppression of speckle noise, but also makes it possible to, using light emitted from a small light-emitting point, narrow a line width of linear light to a desired size described in detail later. Consequently, a surface shape of a strip-shaped body made of a metallic body can be measured with higher precision.

Note that in order to suppress occurrence of speckle noise, in a display device such as a projector, a plurality of semiconductor lasers each having a wide spectral half-width and having different emission wavelengths are used to achieve a plurality of light-emitting points, and beams of light of different wavelengths from the respective light-emitting points are overlapped with each other, in some cases. However, in such a method using semiconductor lasers, the line width of linear light generated from laser light cannot be narrowed, and the method cannot be applied to a use focused on in the present embodiment, which is to measure a surface shape of a strip-shaped body made of a metallic body with high precision.

In addition, it may be possible to use a laser light source capable of achieving a single light-emitting point in order to adjust a line width of linear light. However, with laser light, a spectral half-width is narrow and consequently cannot achieve the spectral half-width described above, and speckle noise cannot be suppressed. It may also be possible to use an LED as a light source capable of achieving a single light-emitting point with a wide spectral half-width. However, with an LED, the line width of generated linear light cannot be narrowed because the light-emitting point is large, and the LED cannot be applied to a use focused on in the present embodiment, which is to measure a surface shape of a strip-shaped body made of a metallic body with high precision.

[Upper Limit of Wavelength of Linear Light]

An upper limit value of a wavelength of linear light applied from the linear light source 101 is prescribed by characteristics of an image sensor that is mounted on the area camera 105 used in the strip-shaped body image capturing apparatus 100. An image sensor generally used, such as a CCD or a CMOS, is formed using a semiconductor material, such as Si or InGaAs, and these semiconductor materials cannot detect light of a wavelength greater than 1700 nm. Therefore, the upper limit value of a wavelength of linear light applied from the linear light source 101 according to the present embodiment is set to 1700 nm.

[Angle of Incidence of Linear Light, Lower Limit of Wavelength of Linear Light, and Line Width on Surface of Strip-Shaped Body]

Now, description will be given on an angle of incidence of linear light, a lower limit of a wavelength of linear light, and a line width on the surface of the strip-shaped body.

As illustrated in FIG. 6, an angle θ formed by the optical axis of the linear light source 101 and the direction normal to the surface of the strip-shaped body S is an angle of incidence θ of linear light. In addition, as schematically illustrated in FIG. 7, linear light applied from the linear light source 101 is assumed to have a finite line width W. On this occasion, when linear light with this line width is incident on the surface of the strip-shaped body S at the angle of incidence θ, linear light is assumed to have a line width of LW on the surface of the strip-shaped body S.

Upper Limit of Angle of Incidence of Linear Light and Upper Limit of Line Width on Surface of Strip-Shaped Body The line width LW on the surface of the strip-shaped body S, which is schematically illustrated in FIG. 7, is set in accordance with how fine the surface shape to be measured is. The size of a fine surface shape to be detected (the degree of spread in the conveyance direction in regard to a peculiar portion of the shape at a surface position (height) of the strip-shaped body S), which is focused on in the shape measurement apparatus 10 according to the present embodiment, is approximately 2 mm at maximum. Therefore, the line width LW of linear light on the surface of the strip-shaped body S illustrated in FIG. 7 is set to be 2 mm at maximum.

In addition, at present, a lower limit value of the line width W of a ray that is industrially achievable in practice in a wavelength band focused on in the present invention is approximately 70 μm. Therefore, in order to achieve line width LW=2 mm on the surface of the strip-shaped body S, the angle of incidence θ is arccos(70 μm/2000 μm)≈88 degrees. Moreover, it is apparent from the geometric relationship illustrated in FIG. 7 that an angle of incidence θ of greater than 88 degrees leads to a line width LW of greater than 2 mm. Hence, in the strip-shaped body image capturing apparatus 100 according to the present embodiment, an upper limit value of an allowable angle of incidence θ of linear light is preferably set to 88 degrees.

FIG. 8 shows, as a table, a result of whether fine unevenness was able to be detected as displacement of a reflected image on a screen in the case where fine unevenness with a diameter of 2 mm was formed on the surface of a steel sheet and then the fine unevenness was observed with the angle of incidence θ of linear light changed. The result shown in FIG. 8 demonstrated that in the case where the angle of incidence θ was 88 degrees or less and the line width LW on the surface of the strip-shaped body was 2 mm or less, fine unevenness with a diameter of 2 mm was able to be detected. On the other hand, in the case where the angle of incidence θ was greater than 88 degrees and the line width LW on the surface of the strip-shaped body was greater than 2 mm, fine unevenness with a diameter of 2 mm was not able to be detected. Such a change in detection performance of fine unevenness due to a change in angle of incidence also demonstrates that a maximum value of the angle of incidence θ is preferably set to 88 degrees in the strip-shaped body image capturing apparatus 100 according to the present embodiment.

Lower Limit of Angle of Incidence of Linear Light and Lower Limit of Wavelength

As mentioned above, the shape measurement apparatus 10 according to the present embodiment measures a surface shape of a strip-shaped body on the basis of the principle of an optical lever. To achieve this, linear light applied to the surface of the strip-shaped body needs to be reflected off the surface of the strip-shaped body to be projected on a screen. Hence, in the strip-shaped body image capturing apparatus 100 according to the present embodiment, it is important to control an angle of incidence of linear light and a wavelength of linear light so that the surface of a metallic body, which often originally does not have specularity, can be regarded as a specular surface.

As described in Non-Patent Literature 1, the influence of surface roughness of a measurement object and a wavelength of light used for measurement exerted on specularity of the surface of the measurement object can be discussed on the basis of a parameter g expressed by Formula 1 below.

[Math. 5]

$$g = \left(\frac{4\pi\sigma}{\lambda}\cos\theta\right)^2 \quad \text{(Formula 1)}$$

Here, in Formula 1 above,
σ: standard deviation of unevenness on surface of measurement object [μm];
θ: angle of incidence [degree]; and
λ: wavelength of light used for measurement [μm].

Since it is known that a diffuse reflection component rapidly increases in the case where the parameter g expressed by Formula 1 above satisfies g>1, in the strip-shaped body image capturing apparatus 100 according to the present embodiment, it is important that the parameter g be 1 or less. The standard deviation σ of fine unevenness to be detected on the surface of a measurement object, which is focused on in the shape measurement apparatus 10 according to the present embodiment, is approximately 0.5 μm at maximum; therefore, in the strip-shaped body image capturing apparatus 100 according to the present embodiment, the angle of incidence θ and the wavelength λ of linear light need to satisfy Formula 3 below. Hence, in the strip-shaped body image capturing apparatus 100 according to the present embodiment, the angle of incidence θ of linear light and the wavelength λ of linear light are placed so as to satisfy Formula 3 below related to specularity of a strip-shaped body.

[Math. 6]

$$\frac{\cos\theta}{\lambda} \leq \frac{1}{2\pi} \approx 0.16 \quad \text{(Formula 3)}$$

Formula 3 above is put into a graph as shown in FIG. 9.

At 88 degrees, which is the upper limit value of the angle of incidence θ, a wavelength that guarantees parameter g≤1 is about 200 nm according to Formula 3 and FIG. 9. A superluminescent diode used as the linear light source 101 according to the present embodiment often has an emission wavelength λ of 800 nm or more. Therefore, parameter g≤1 is guaranteed by using a superluminescent diode and setting the angle of incidence θ to 88 degrees, as is apparent from FIG. 9. On the other hand, at 1700 nm, which is the upper limit of a wavelength of linear light, the magnitude of the angle of incidence θ that guarantees parameter g≤1 is about 74 degrees according to Formula 3 and FIG. 9. Hence, in the strip-shaped body image capturing apparatus 100 according to the present embodiment, the lower limit of the angle of incidence is preferably set to 74 degrees.

Next, in the shape measurement apparatus 10 according to the present embodiment, when a minimum value of a size of a fine surface shape to be detected is denoted by $L_{min}$, an upper limit value of the line width LW on the surface of the strip-shaped body, which is illustrated in FIG. 7, is $L_{min}$. It is apparent from the geometric relationship illustrated in FIG. 7 that LW cos θ=W; therefore, it is required that a relationship expressed by Formula 5 below hold.

[Math. 7]

$$L_{min} \geq LW = \frac{W}{\cos\theta} \quad \text{(Formula 5)}$$

Formula 5 above is transformed into Formula 5' below, and a lower limit value of the angle of incidence θ is prescribed on the basis of Formula 5'. On the other hand, on the basis of Formula 3 above, the upper limit value of the angle of incidence θ is prescribed as in Formula 3' below. Hence, according to Formula 3' and Formula 5' below, the line width W of linear light along the longitudinal direction of the strip-shaped body is preferably controlled to satisfy Formula 7 below, according to the minimum value $L_{min}$ of a size of a surface shape to be measured along the longitudinal direction and the wavelength λ of linear light.

[Math. 8]

$$\cos\theta \geq \frac{W}{L_{min}} \quad \text{(Formula 5')}$$

$$\cos\theta \leq \frac{\lambda}{2\pi} \quad \text{(Formula 3')}$$

$$\frac{W}{L_{min}} \leq \frac{\lambda}{2\pi} \quad \text{(Formula 7)}$$

According to the above discussion, it is found that, in the strip-shaped body image capturing apparatus 100 according to the present embodiment, (1) it is important that the angle of incidence θ of linear light and the wavelength λ of linear light be placed so as to satisfy Formula 3 above related to specularity of a strip-shaped body, (2) the line width W of linear light along the longitudinal direction of the strip-shaped body is preferably controlled to satisfy Formula 7 above, according to the minimum value $L_{min}$ of a size of a surface shape to be measured along the longitudinal direction and the wavelength of linear light, (3) a wavelength of linear light is preferably equal to or greater than 800 nm and equal to or less than 1700 nm, and (4) the linear light source is preferably placed on the basis of Formula 3 above in a manner that the angle of incidence θ falls within a range of equal to or greater than 74 degrees and equal to or less than 88 degrees. The angle of incidence θ of linear light on the surface of the strip-shaped body S is preferably in a range of 80 degrees to 88 degrees.

By using linear light satisfying the conditions described above, the strip-shaped body image capturing apparatus 100 according to the present embodiment can capture an image of a change in an extremely fine surface shape with a height of approximately several micrometers and a size of approximately 2 mm with high precision, while preventing occurrence of speckle noise.

[Power Density of Linear Light on Surface of Strip-Shaped Body]

By using linear light satisfying the conditions described above, the strip-shaped body image capturing apparatus 100 according to the present embodiment can perform an image capturing process with high precision, while preventing occurrence of speckle noise. On this occasion, power density of linear light on the surface of the strip-shaped body is set within a range mentioned below; thus, on the projection plane of the screen 103, luminance of reflected light of linear light can be higher, which enables a more reliable image capturing process.

The present inventors installed the strip-shaped body image capturing apparatus 100 illustrated in FIG. 2 in a production line of a steel sheet operated at a line speed of 180 mpm=3000 mm/sec, and captured one image per 1-mm pitch of movement amount of the steel sheet. Exposure time at this time was 1 mm/(3000 mm/sec)=0.33 msec. At this time, on the surface of the steel sheet, the present inventors performed an experiment while changing intensity of linear light, using a light source with a line length (a length in the width direction in FIG. 2) of 160 mm and a line width (the line width W in FIG. 7) of 70 μm. In this case, when the output of the light source was 55 mW or more, an image of reflected light was observed with sufficient luminance on the projection plane of the screen 103.

Power density of linear light on the surface of the strip-shaped body S (more specifically, on a plane perpendicular to an optical axis of linear light on the surface of the strip-shaped body S) in this case is 55 mW/(160 mm×70 μm)=491 mW/cm².

In a production line of the strip-shaped body S, which is focused on in the present embodiment, complete stop of the production line is undesirable for securing continuity of material properties of the strip-shaped body S, and it is important to maintain a line speed of 20 mpm at minimum. Hence, power density of linear light that enables measurement of a surface shape at this line speed is 491 (mW/cm²)÷(180 mpm/20 mpm)=55 mW/cm².

According to the finding described above, in order to make luminance of reflected light of linear light higher on the projection plane of the screen 103 to enable a more reliable image capturing process, power density of linear light on the surface of the strip-shaped body is preferably set to 55 mW/cm² or more. In addition, power density of linear light on the surface of the strip-shaped body is preferably as large as possible, as long as no problem occurs on the surface of the strip-shaped body S, and increasing power density of linear light makes it possible to perform an image capturing process reliably even in higher-speed production lines. Power density of linear light on the surface of the strip-shaped body is further preferably 491 mW/cm² or more, still further preferably 982 mW/cm² or more.

Power density of linear light on the surface of the strip-shaped body S of 491 mW/cm² or more is further preferred in consideration of the test result at a line speed of 180 mpm described above. Power density of 982 mW/cm² or more is still further preferred because the line speed may rise to 360 mpm depending on a change in operation state of the line. Note that in regard to power density, there is no upper limit value for exerting an effect of the invention in the present embodiment. This is because, although linear light in a captured image appears thick and measurement precision decreases if power density is too high, appropriate image capturing luminance can be easily achieved by shortening exposure time.

The linear light source 101 included in the strip-shaped body image capturing apparatus 100 according to the present embodiment has been described in detail with reference to FIGS. 5 to 9.

<Surface Roughness of Projection Plane of Screen 103>

By satisfying the conditions described above, the strip-shaped body image capturing apparatus 100 according to the present embodiment can obtain linear light not including speckle noise, which enables a more reliable image capturing process. On this occasion, using the screen 103 having a projection plane described below enables a more clear captured image to be obtained, and makes it possible to perform measurement with higher precision.

In the present embodiment, surface roughness of the projection plane of the screen 103 is evaluated using a mean width RSm of roughness profile elements prescribed in JIS B0601:2001 (standard corresponding to ISO4287:1997). As schematically illustrated in FIG. 10, a mean width RSm of roughness profile elements prescribed in JIS B0601:2001 expresses the mean of widths of profile (roughness profile) elements in a reference length Lr of a roughness profile. Hence, in the case where N profile elements are present in the reference length Lr, the mean width RSm of the roughness profile elements is a value expressed by Formula 11 below. Here, in Formula 11, Xsi is the width of the i-th profile element.

[Math. 9]

$$Rsm = \frac{1}{N} \cdot \sum_{i=1}^{N} Xsi \quad \text{(Formula 11)}$$

Here, in JIS B0601:2001, a minimum height and a minimum width are prescribed for peaks (valleys) constituting a profile element. That is, if a peak height (valley depth) is 10% or less of a maximum height or a width of an element is 1% or less of a length of a calculation section, the element is regarded as noise and treated as part of a valley (peak) preceding or following the element.

In the example illustrated in FIG. 10, five profile elements are present in the reference length Lr, and RSm=(Xs1+Xs2+Xs3+Xs4+Xs5)/5 is obtained using widths Xs1 to Xs5 of the profile elements.

In the present embodiment, surface unevenness of the projection plane of the screen 103 is observed using a known roughness meter, and a roughness profile of the projection plane of the screen was obtained. On this occasion, the mean width RSm of the roughness profile elements related to the projection plane of the screen 103 according to the present embodiment is preferably 10 times or more greater than a wavelength of linear light, and $\frac{1}{10}$ or less of a line width of reflected light of linear light along the height direction of the screen on the screen 103.

In the case where the mean width RSm of the roughness profile elements is less than 10 times the wavelength of linear light, reflected light of linear light is regularly reflected in a higher proportion on the projection plane of the screen 103, which may reduce the amount of light received by the area camera 105. Moreover, in the case where the mean width RSm of the roughness profile elements is greater than $\frac{1}{10}$ of the line width of reflected light of linear light along the height direction of the screen on the screen 103, surface roughness of the projection plane of the screen 103 is too large, which increases the tendency of irregularity due to surface roughness of the screen to occur in an image of reflected light of linear light.

In the strip-shaped body image capturing apparatus 100 according to the present embodiment, the screen 103 having the surface roughness described above can be used more favorably. Such a screen 103 is not particularly limited, but for example, a screen provided with a metal oxide such as $Al_2O_3$ on the surface can be used.

The strip-shaped body image capturing apparatus 100 according to embodiments of the present invention has been described in detail with reference to FIGS. 2 to 10.

Note that the strip-shaped body image capturing apparatus 100 according to the present embodiment, which is described above, can be installed at any position of a conveyor line that conveys the strip-shaped body S according to the present embodiment, as long as an image capturing process is not physically hindered. In addition, the strip-shaped body image capturing apparatus 100 according to the present embodiment is preferably installed in an area where the strip-shaped body S is positioned on the surface of a roll having a predetermined curvature (in other words, an area where the strip-shaped body S is wound around a roll having a predetermined curvature). In that case, the linear light described above is applied to the surface of the strip-shaped body positioned on the surface of the roll having the predetermined curvature. Installing the strip-shaped body image capturing apparatus 100 in such an area can suppress vibration of the strip-shaped body S accompanying conveyance, and enable an image capturing process with higher precision.

(Arithmetic Processing Apparatus 200)

<Overall Configuration of Arithmetic Processing Apparatus 200>

Figure 11:
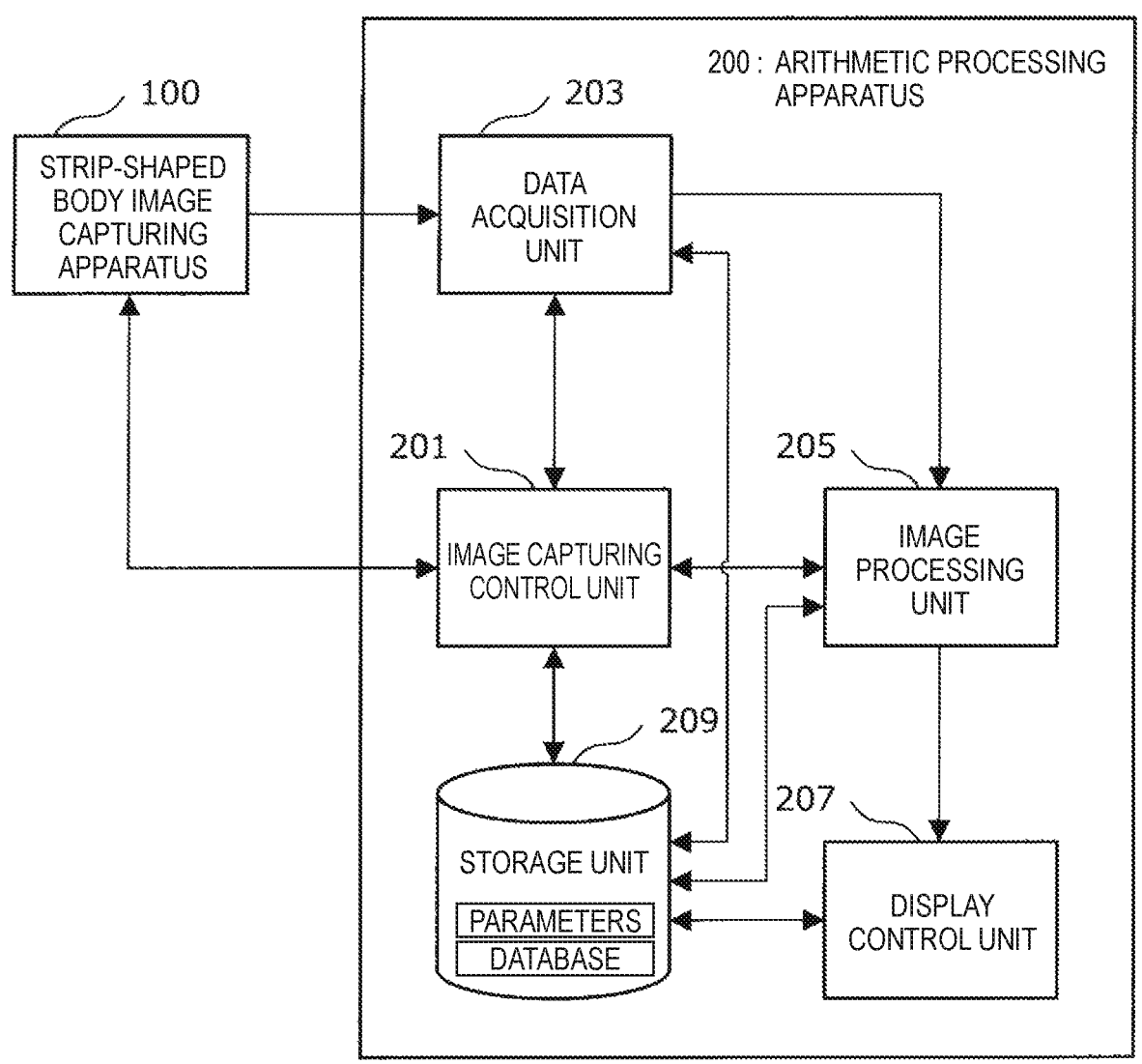
FIG. 11 is a block diagram illustrating an example of a configuration of an arithmetic processing apparatus included in a shape measurement apparatus according to the embodiment.

Now, an overall configuration of the arithmetic processing apparatus 200 according to the present embodiment will be described in detail with reference to FIG. 11. FIG. 11 is a block diagram illustrating an example of a configuration of an arithmetic processing apparatus included in a shape measurement apparatus according to the present embodiment.

As illustrated in FIG. 11, the arithmetic processing apparatus 200 according to the present embodiment mainly includes an image capturing control unit 201, a data acquisition unit 203, an image processing unit 205, a display control unit 207, and a storage unit 209.

The image capturing control unit 201 is configured with, for example, a central processing unit (CPU), a read only memory (ROM), a random access memory (RAM), a communication device, and the like. The image capturing control unit 201 controls, in a centralized manner, an image capturing process of reflected light of linear light by the strip-shaped body image capturing apparatus 100 according to the present embodiment.

Specifically, in starting the image capturing of reflected light of linear light, the image capturing control unit 201 sends a controls signal for starting application from the linear light source 101 to the strip-shaped body image capturing apparatus 100. In addition, when the strip-shaped body image capturing apparatus 100 starts image capturing of reflected light projected on the screen 103, the image capturing control unit 201 sends a trigger signal for starting image capturing to the area camera 105 each time a PLG signal sent at regular intervals from a driving mechanism or the like that controls conveyance of the strip-shaped body S (for example, a PLG signal output each time the rigid body S moves 1 mm) is acquired.

The data acquisition unit 203 is configured with, for example, a CPU, a ROM, a RAM, a communication device, and the like. The data acquisition unit 203 acquires captured image data output from the strip-shaped body image capturing apparatus 100. The data acquisition unit 203 outputs the acquired captured image data to the image processing unit 205 described later.

The image processing unit 205 is configured with, for example, a CPU, a ROM, a RAM, a communication device, and the like. The image processing unit 205 acquires image capturing image capturing data generated by the area camera 105, performs image processing described later on the image capturing data, and calculates a surface shape of the strip-shaped body S. Upon ending the calculation process for the surface shape of the strip-shaped body S, the image processing unit 205 transmits information on the obtained calculation results to the display control unit 207 and the storage unit 209, and transmits the information to various devices provided outside the shape measurement apparatus 10.

This image processing unit 205 will be described in detail later.

The display control unit 207 is configured with, for example, a CPU, a ROM, a RAM, an output device, a communication device, and the like. The display control unit 207 performs display control in displaying measurement results of the strip-shaped body S, which are transmitted from the image processing unit 205, on an output device (e.g., a display) included in the arithmetic processing apparatus 200, an output device provided outside the arithmetic processing apparatus 200, or the like. Thus, a user of the shape measurement apparatus 10 can recognize on-site measurement results related to the surface shape of the strip-shaped body S.

The storage unit 209 is an example of a storage device included in the arithmetic processing apparatus 200, and is configured with, for example, a ROM, a RAM, a storage device, and the like. In the storage unit 209, information on design parameters of the shape measurement apparatus 10 is contained, such as information indicating an optical positional relationship between the linear light source 101 and the area camera 105 included in the strip-shaped body image capturing apparatus 100, and information transmitted from a host computer (e.g., a management computer that manages the conveyor line as a whole) provided outside the shape measurement apparatus 10. In addition, in the storage unit 209, various parameters and process intermediate progresses that the arithmetic processing apparatus 200 according to the present embodiment needs to save when performing some sort of process (e.g., measurement results transmitted from the image processing unit 205, various data and databases contained beforehand, and programs) are recorded as appropriate. With regard to this storage unit 209, the image capturing control unit 201, the data acquisition unit 203, the image processing unit 205, the display control unit 207, the host computer, and the like can perform a data reading/writing process freely.

<Image Processing Unit 205>

Next, the image processing unit 205 included in the arithmetic processing apparatus 200 according to the present embodiment will be described in detail with reference to FIGS. 12 to 15.

Figure 12:
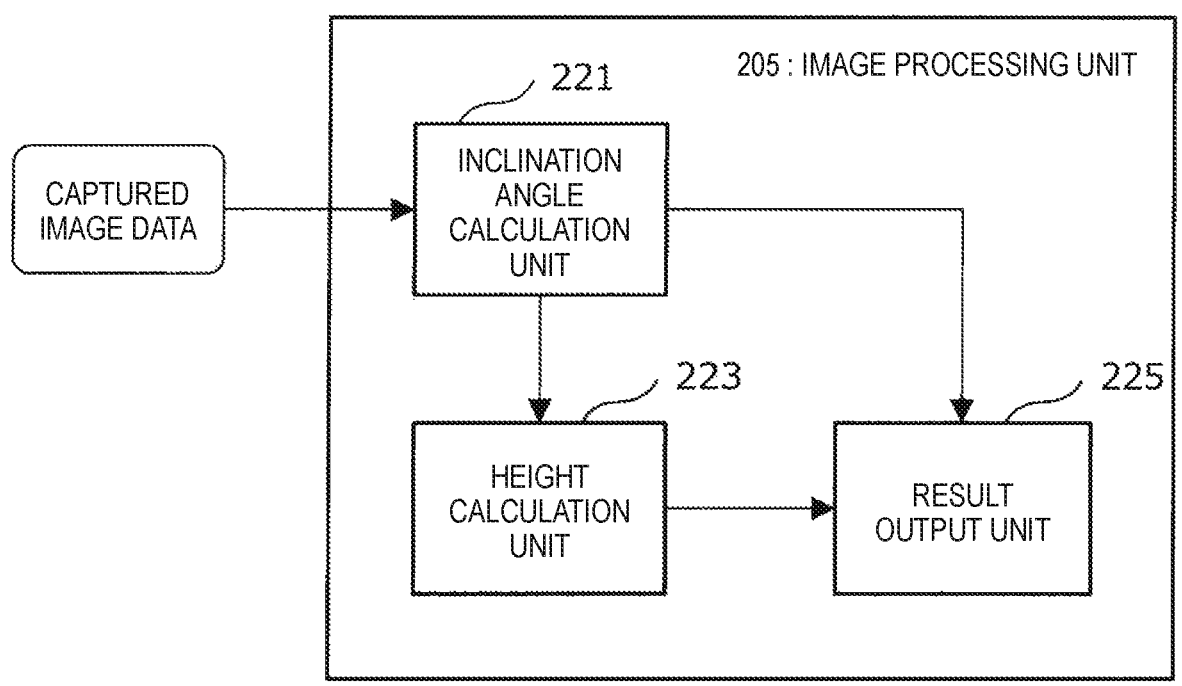
FIG. 12 is a block diagram illustrating an example of a configuration of an image processing unit included in an arithmetic processing apparatus according to the embodiment.
Figure 13:
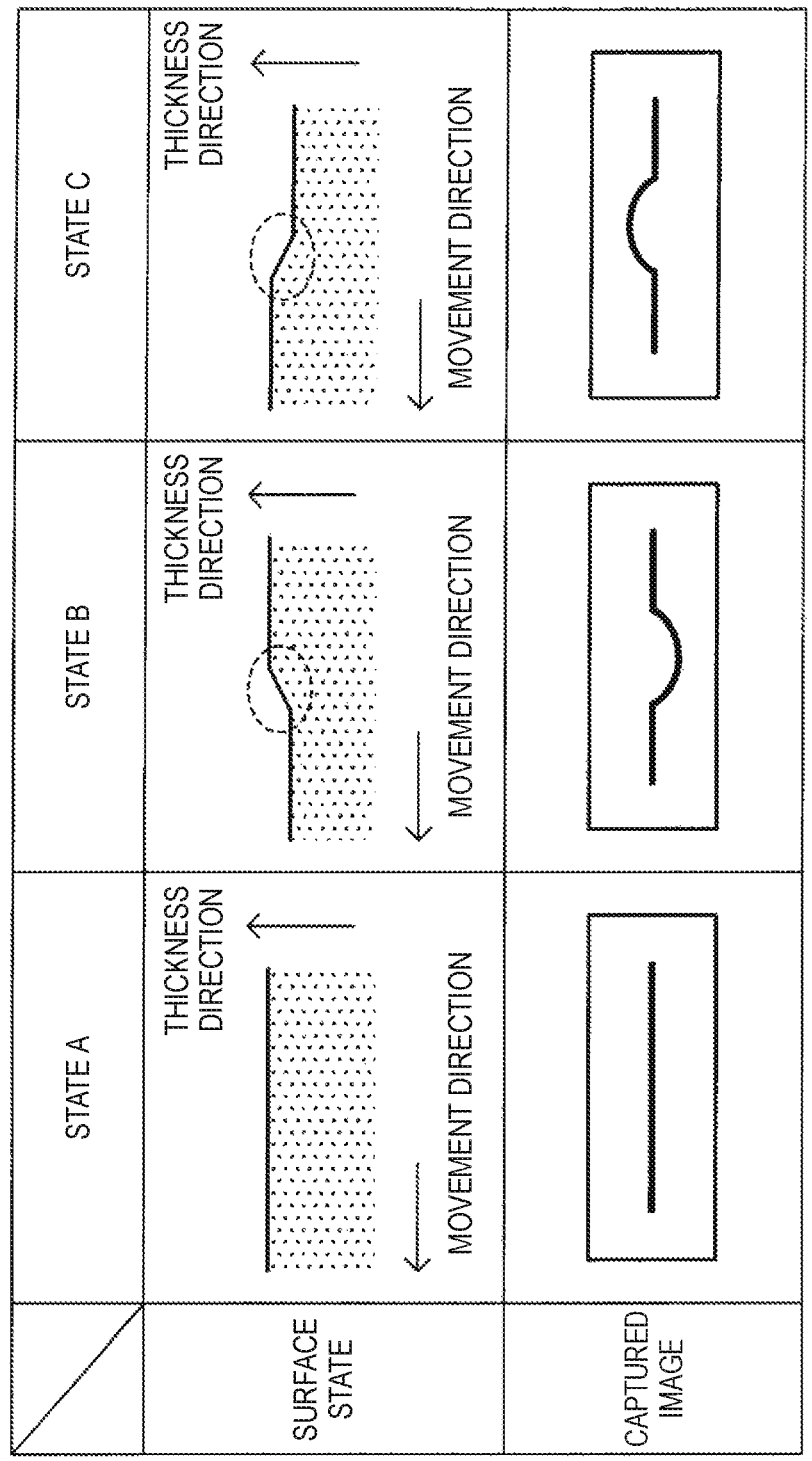
FIG. 13 is an explanatory diagram schematically illustrating the relationship between a surface state of a strip-shaped body and a captured image.
Figure 14:
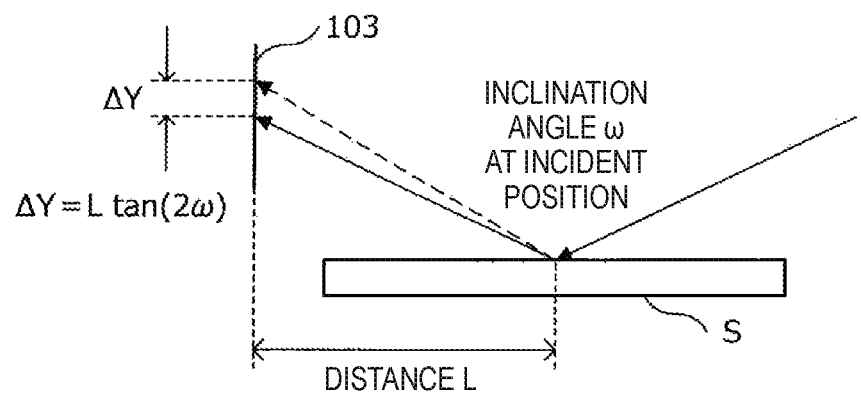
FIG. 14 is an explanatory diagram schematically illustrating the relationship between an inclination of the surface of a strip-shaped body and an amount of displacement of reflected light on a projection plane of a screen.
Figure 15:
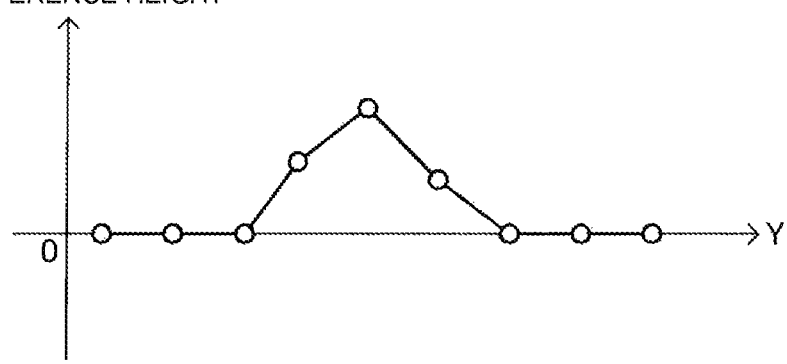
FIG. 15 is an explanatory diagram for a height calculation process performed in an image processing unit according to the embodiment.

FIG. 12 is a block diagram illustrating an example of a configuration of the image processing unit 205 included in an arithmetic processing apparatus according to the present embodiment. FIG. 13 is an explanatory diagram schematically illustrating the relationship between a surface state of a strip-shaped body and a captured image, and FIG. 14 is an explanatory diagram schematically illustrating the relationship between an inclination of the surface of a strip-shaped body and an amount of displacement of reflected light on a projection plane of a screen. FIG. 15 is an explanatory diagram for a height calculation process performed in an image processing unit according to the present embodiment.

The image processing unit 205 according to the present embodiment uses a captured image generated by the strip-shaped body image capturing apparatus 100, and performs image processing on this captured image to calculate information on the surface shape of the strip-shaped body S. The image processing unit 205 includes, as illustrated in FIG. 12, an inclination angle calculation unit 221, a height calculation unit 223, and a result output unit 225.

The inclination angle calculation unit 221 is configured with, for example, a CPU, a ROM, a RAM, and the like. The inclination angle calculation unit 221 uses a captured image generated by the strip-shaped body image capturing apparatus 100 to calculate an inclination angle $\omega$ of the surface of the strip-shaped body S, as information on the surface shape of the strip-shaped body S. Detailed description will be given on a calculation process of the inclination angle $\omega$ of the surface performed by the inclination angle calculation unit 221.

The inclination angle calculation unit 221 according to the present embodiment calculates the inclination angle $\omega$ of the surface of the strip-shaped body S on the basis of a degree of bend of a reflected image of linear light in the captured image.

As schematically illustrated as a state A in FIG. 13, in the case where the surface of the strip-shaped body S in an area irradiated with linear light is flat, a reflected image of linear light in a captured image is substantially straight along the width direction of the screen. As schematically illustrated as a state B in FIG. 13, in the case where the surface of the strip-shaped body S is inclined downward toward the movement direction in an area irradiated with linear light (a region surrounded by a broken line in the drawing), a reflected image of linear light reflected off this inclined surface is displaced downward in the height direction of the screen from a position (hereinafter also referred to as "reference position") of a reflected image in a flat portion. Consequently, as illustrated in the state B in FIG. 13, a straight portion substantially parallel to the width direction of the screen and a downwardly convex portion are mixed in the captured image. In contrast, as schematically illustrated as a state C in FIG. 13, in the case where the surface of the strip-shaped body S is inclined upward toward the movement direction in an area irradiated with linear light (a region surrounded by a broken line in the drawing), a reflected image of linear light reflected off this inclined surface is displaced upward in the height direction of the screen from a position of a reflected image in a flat portion. Consequently, as illustrated in the state C in FIG. 13, a straight portion substantially parallel to the width direction of the screen and an upwardly convex portion are mixed in the captured image.

An amount of displacement of the reflected image from the reference position, which is schematically illustrated in the state B and the state C in FIG. 13, is proportional to the magnitude of the inclination angle $\omega$ of the surface of the strip-shaped body S. Hence, the inclination angle calculation unit 221 first specifies a position with a maximum value of luminance distribution in the height direction of the screen 103 (hereinafter also referred to as "Y direction") in a captured image by center-of-gravity operation using luminance values, and sets the position as the center of a line width of the reflected image. Then, the inclination angle calculation unit 221 specifies a change in the center position of the line width of the reflected image along the width direction of the screen 103 (hereinafter also referred to as "X direction") in the captured image. Thus, the inclination angle calculation unit 221 can specify, at each X coordinate in the captured image, a difference (i.e., an amount of displacement $\Delta Y$ from the reference position) with respect to the reference position (i.e., a Y coordinate in a straight portion substantially parallel to the width direction of the screen).

Displacement of a reflected image in a captured image is caused by a change in surface shape that is larger than the line width LW of linear light, and linear light reflected off the surface of the strip-shaped body S where a change in surface shape that is larger than the line width LW of linear light has occurred goes upward or downward on the projection plane of the screen 103 in accordance with a direction and an angle of an inclination of this portion. Here, the relationship between the amount of displacement $\Delta Y$ of the reflected image from the reference position in the captured image and the inclination angle $\omega$ of the surface shape of the strip-shaped body S is given by $\Delta Y = \tan 2\omega$ as illustrated in FIG. 14, on the basis of the principle of an optical lever. Here, L is a horizontal distance from a point of incidence of linear light on the strip-shaped body S to the screen 103. Hence, the inclination angle $\omega$ of the surface of interest can be calculated by performing an operation of $\omega = (\frac{1}{2}) \times \tan^{-1}(\Delta Y/L)$. On this occasion, since the horizontal distance L can be recognized beforehand as a design parameter of the strip-shaped body image capturing apparatus 100, the inclination angle calculation unit 221 can calculate the inclination angle $\omega$ using the amount of displacement $\Delta Y$ from the reference position obtained by analyzing the captured image.

By performing the process described above, the inclination angle calculation unit 221 can obtain distribution of an inclination of the surface of the strip-shaped body S in an area irradiated with linear light. A data group of inclination values obtained in this manner serves as information for inspection used in inspecting the shape (specifically, surface shape) of the strip-shaped body S. Here, the information for inspection can be imaged by replacing inclination values included in the information for inspection with high/low of luminance values or light/dark. By collectively imaging the generated data on inclination angles for a plurality of captured images into an inclination image, shape inspection based on the inclination image can be performed.

Moreover, the inclination angle calculation unit 221 can perform inspection of the surface shape of the strip-shaped body S by comparing the calculated inclination angle with a predetermined threshold value. That is, a threshold value of the inclination angle of the surface when an abnormal portion is present at the surface of the strip-shaped body S is specified in advance by performing known statistical processing or the like on the basis of operation data in the past, etc., and contained in the storage unit 209 or the like. Then, the inclination angle calculation unit 221 specifies the magnitude relation between the calculated inclination angle value and the threshold value, which makes it possible to inspect whether an abnormal portion is present at the surface of the strip-shaped body S of interest.

Furthermore, since a change in luminance due to speckle noise is not overlapped on the captured image generated by the strip-shaped body image capturing apparatus 100 according to the present embodiment, it is presumed that a change in luminance of a reflected image in the captured image is caused by a change in shape present on the surface of the strip-shaped body S or dirt attached to the surface of the strip-shaped body S. Hence, the inclination angle calculation unit 221 can precisely distinguish between a change in surface shape and harmless dirt, in total consideration of information on the inclination angle specified in the above-described manner and a change in luminance value in the captured image.

The inclination angle calculation unit 221 outputs the data on an inclination angle of the surface of the strip-shaped body S generated in the above-described manner to the height calculation unit 223. In addition, the inclination angle calculation unit 221 may output the generated data on an inclination angle of the surface of the strip-shaped body S itself, or inspection results of the surface of the strip-shaped body S to the result output unit 225.

The height calculation unit 223 is configured with, for example, a CPU, a ROM, a RAM, and the like. The height calculation unit 223 calculates the height of the surface of the strip-shaped body S of interest as information on the surface shape of the strip-shaped body S by using the inclination angle of the surface of the strip-shaped body S calculated by the inclination angle calculation unit 221. Specifically, the height calculation unit 223 integrates a tangent tan $\omega$ of the inclination angle along the movement direction of the strip-shaped body S (in other words, the Y direction in the captured image) as illustrated in FIG. 15 by using the inclination angle ω of the surface of the strip-shaped body S calculated by the inclination angle calculation unit 221, thereby calculating the height of the surface of the strip-shaped body S (a difference value with respect to a reference height).

By performing the above-described integrating process for all elements of the data on the inclination angles of the surface obtained from the captured images, the height calculation unit 223 can obtain a data group on surface heights (in other words, map data on surface heights) for the entire surface of the strip-shaped body S. The data group on surface heights obtained in this manner serves as information for inspection used in inspecting the shape (specifically, surface shape) of the strip-shaped body S. Here, the information for inspection can be imaged by replacing surface height values included in the information for inspection with high/low of luminance values or light/dark. By imaging the generated map data on surface heights into a height image, the height calculation unit 223 can perform shape inspection based on the height image.

The height calculation unit 223 outputs the data on the height of the surface of the strip-shaped body S generated in the above-described manner to the result output unit 225.

The result output unit 225 is configured with, for example, a CPU, a ROM, a RAM, an output device, and the like. The result output unit 225 outputs various types of information on surface shapes of the strip-shaped body S generated by the inclination angle calculation unit 221 and the height calculation unit 223, to the display control unit 207. Thus, various types of information on measurement results of the surface shape of the strip-shaped body S is output to a display unit (not illustrated), such as a display. The result output unit 225 may also output the obtained calculation results of the surface shape to an external device such as a process computer for production management, and may create various record files related to products by utilizing the obtained shape calculation results. Moreover, the result output unit 225 may contain information on the surface shape of the strip-shaped body S, as history information, in the storage unit 209 or the like, in association with time information on date and time at which the information is calculated.

An example of the function of the arithmetic processing apparatus 200 according to the present embodiment has been illustrated. Each of the above structural elements may be configured with a general-purpose member or circuit, and may be configured with hardware specialized for the function of each structural element. A CPU or the like may perform all of the functions of respective structural elements. Thus, a utilized configuration can be changed as appropriate, according to the technology level at the time of performing the present embodiment.

Note that the computer program for providing each function of the arithmetic processing apparatus according to the above present embodiment can be created and implemented in a personal computer or the like. Moreover, a computer-readable recording medium that contains this computer program can be provided as well. For example, the recording medium is a magnetic disk, an optical disc, a magneto-optical disk, a flash memory, or the like. The above computer program may be delivered via a network for example, without using the recording medium.

As described above, according to the shape measurement apparatus 10 according to the present embodiment, a surface shape of the strip-shaped body S can be measured with higher precision on the basis of the principle of an optical lever, by using linear light satisfying a specific condition. In addition, in the shape measurement apparatus 10 according to the present embodiment, linear light satisfying the specific condition is focused on the surface of the strip-shaped body S so as to satisfy a predetermined condition, which can reduce a data reading height of the area camera 105, enabling a further increase in processing speed. Moreover, in the shape measurement apparatus 10 according to the present embodiment, since linear light in which occurrence of speckle noise is prevented is used, a change in inclination of the surface calculated on the basis of the captured image and a change in luminance value in the captured image can be detected independently.

(Sequence of Shape Measurement Method)

Figure 16:
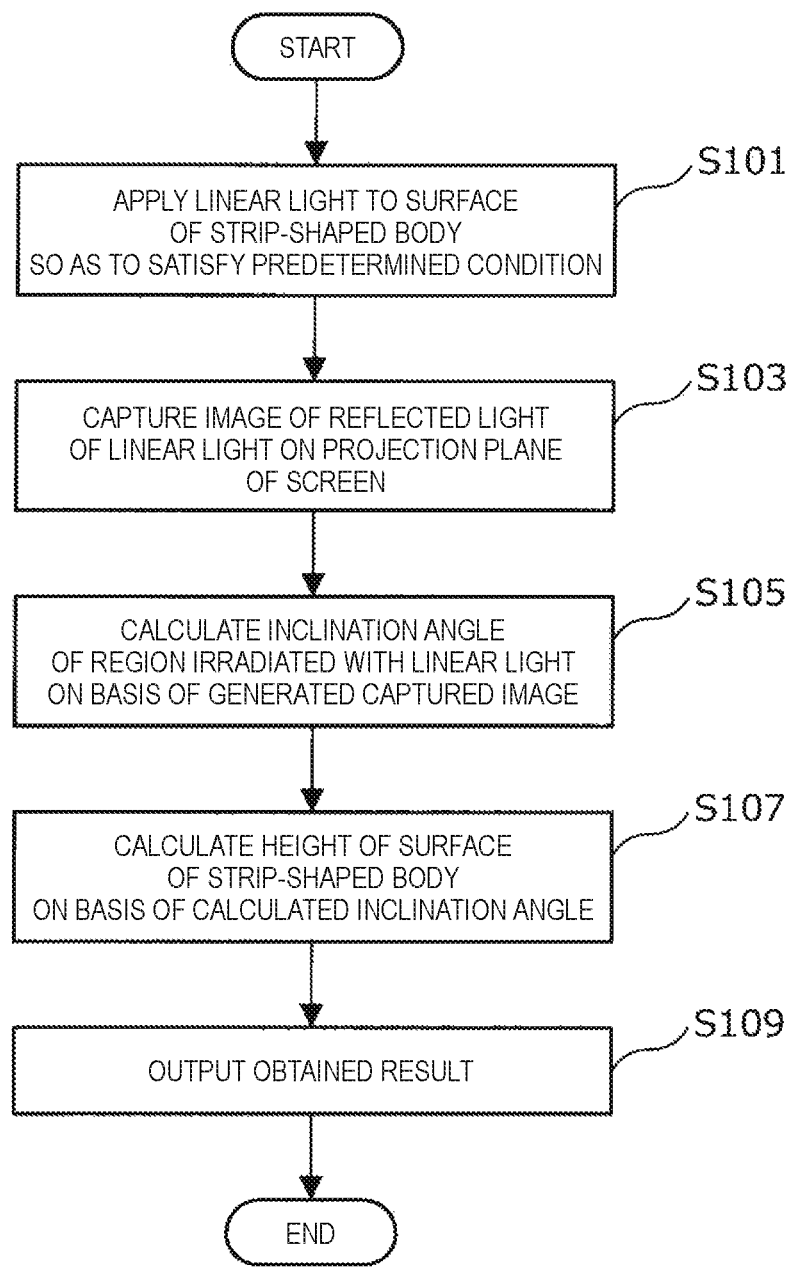
FIG. 16 is a flowchart showing an example of a sequence of a shape measurement method according to the embodiment.

Next, an example of a sequence of a shape inspection method performed in the shape measurement apparatus 10 according to the present embodiment will be described briefly with reference to FIG. 16. FIG. 16 is a flowchart showing an example of a sequence of a shape inspection method according to the present embodiment.

The linear light source 101 of the strip-shaped body image capturing apparatus 100 of the shape measurement apparatus 10, under control of the image capturing control unit 201 of the arithmetic processing apparatus 200, applies linear light described above to the surface of the strip-shaped body S so as to satisfy a predetermined condition (step S101). Then, the area camera 105 of the strip-shaped body image capturing apparatus 100 captures an image of reflected light of linear light on the projection plane of the screen 103 (step S103), and outputs data of the generated captured image to the arithmetic processing apparatus 200.

Upon acquiring the data of the generated captured image output from the strip-shaped body image capturing apparatus 100, the data acquisition unit 203 of the arithmetic processing apparatus 200 outputs the acquired measurement data to the inclination angle calculation unit 221 of the image processing unit 205.

The inclination angle calculation unit 221 calculates data on an inclination angle of the surface of the strip-shaped body S of interest (i.e., an inclination angle of the region irradiated with linear light) by using the captured image generated by the strip-shaped body image capturing apparatus 100 (step S105). After that, the inclination angle calculation unit 221 outputs the calculated data on the inclination angle to the height calculation unit 223.

After that, the height calculation unit 223 integrates a tangent of the inclination angle using the inclination angle contained in the data on the inclination angle output from the inclination angle calculation unit 221, thereby calculating the height of the surface of the strip-shaped body S (step S107). The height calculation unit 223 outputs the obtained data on the height of the surface of the strip-shaped body S to the result output unit 225.

When various types of information for surface shape of the strip-shaped body S is input, the result output unit 225 outputs the obtained information to a user or various devices provided outside (step S109). Thus, the user can recognize various types of information on the shape of the strip-shaped body S.

An example of a sequence of a shape inspection method performed in the shape measurement apparatus 10 according to the present embodiment has been described briefly with reference to FIG. 16.

(Hardware Configuration)

Figure 17:
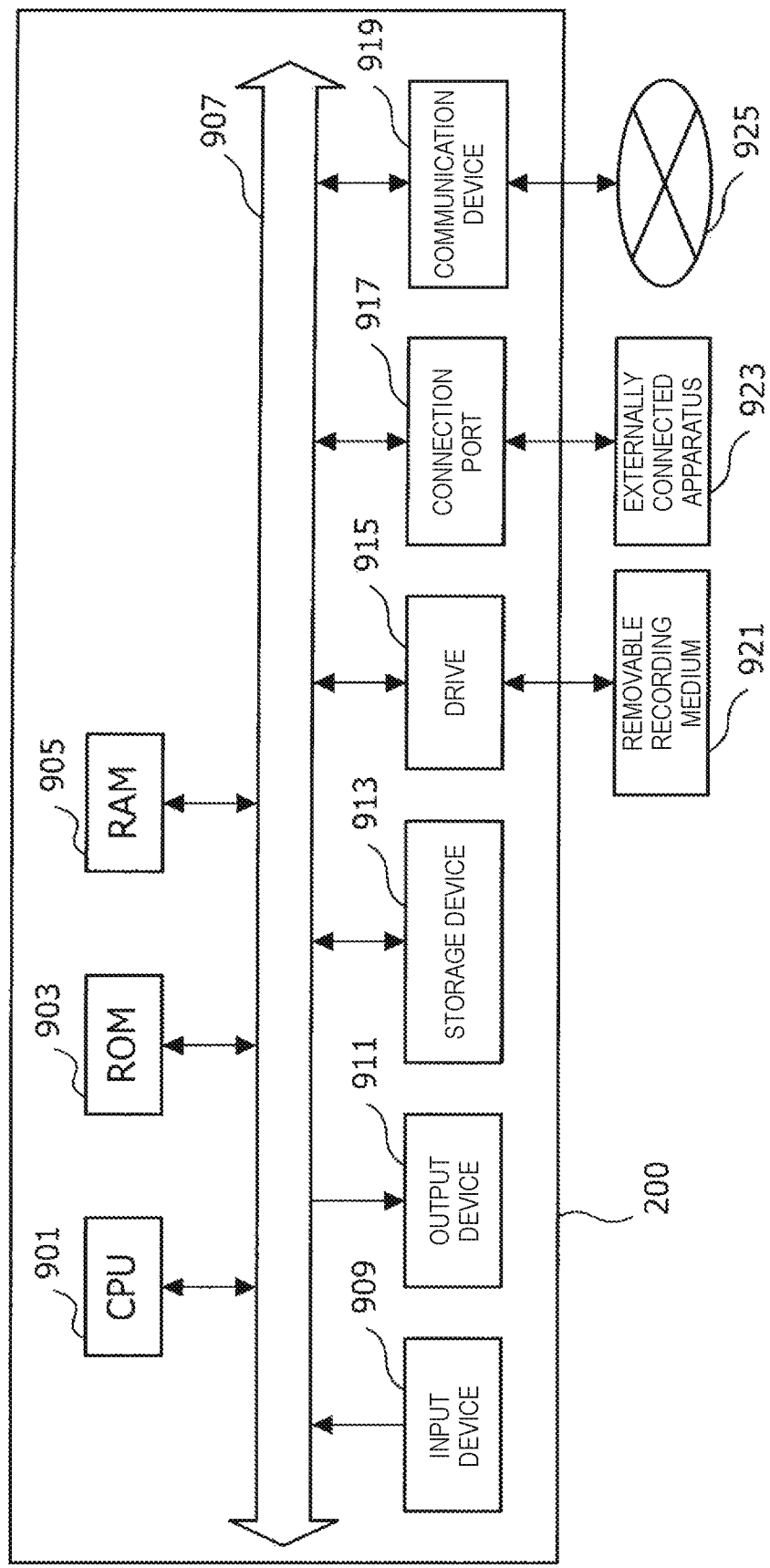
FIG. 17 is a block diagram illustrating an example of the hardware configuration of an arithmetic processing apparatus according to the embodiment.

Next, the hardware configuration of the arithmetic processing apparatus 200 according to embodiments of the present invention will be described in detail with reference to FIG. 17. FIG. 17 is a block diagram for explaining the hardware configuration of the arithmetic processing apparatus 200 according to an embodiment of the present invention.

The arithmetic processing apparatus 200 mainly includes a CPU 901, a ROM 903, and a RAM 905. Furthermore, the arithmetic processing apparatus 200 also includes a bus 907, an input device 909, an output device 911, a storage device 913, a drive 915, a connection port 917, and a communication device 919.

The CPU 901 serves as a central processing apparatus and a control device, and controls the overall operation or a part of the operation of the arithmetic processing apparatus 200 according to various programs recorded in the ROM 903, the RAM 905, the storage device 913, or a removable recording medium 921. The ROM 903 stores programs, operation parameters, and the like used by the CPU 901. The RAM 905 primarily stores programs that the CPU 901 uses and parameters and the like varying as appropriate during the execution of the programs. These are connected with each other via the bus 907 configured from an internal bus such as a CPU bus or the like.

The bus 907 is connected to the external bus such as a PCI (Peripheral Component Interconnect/Interface) bus via the bridge.

The input device 909 is an operation means operated by a user, such as a mouse, a keyboard, a touch panel, buttons, a switch and a lever. The input device 909 may be a remote control means (a so-called remote control) using, for example, infrared light or other radio waves, or may be an externally connected apparatus 923 such as a PDA conforming to the operation of the arithmetic processing apparatus 200. Furthermore, the input device 909 generates an input signal based on, for example, information which is input by a user with the above operation means, and is configured from an input control circuit for outputting the input signal to the CPU 901. The user can input various data to the arithmetic processing apparatus 200 and can instruct the arithmetic processing apparatus 200 to perform processing by operating this input device 909.

The output device 911 is configured from a device capable of visually or audibly notifying acquired information to a user. Examples of such device include display devices such as a CRT display device, a liquid crystal display device, a plasma display device, an EL display device and lamps, audio output devices such as a speaker and a headphone, a printer, a mobile phone, a facsimile machine, and the like. For example, the output device 911 outputs a result obtained by various processes performed by the arithmetic processing apparatus 200. More specifically, the display device displays, in the form of texts or images, a result obtained by various processes performed by the arithmetic processing apparatus 200. On the other hand, the audio output device converts an audio signal such as reproduced audio data and sound data into an analog signal, and outputs the analog signal.

The storage device 913 is a device for storing data configured as an example of a storage unit of the arithmetic processing apparatus 200 and is used to store data. The storage device 913 is configured from, for example, a magnetic storage device such as a HDD (Hard Disk Drive), a semiconductor storage device, an optical storage device, or a magneto-optical storage device. This storage device 913 stores programs to be executed by the CPU 901, various data, and various data obtained from the outside.

The drive 915 is a reader/writer for recording medium, and is embedded in the arithmetic processing apparatus 200 or attached externally thereto. The drive 915 reads information recorded in the attached removable recording medium 921 such as a magnetic disk, an optical disk, a magneto-optical disk, or a semiconductor memory, and outputs the read information to the RAM 905. Furthermore, the drive 915 can write in the attached removable recording medium 921 such as a magnetic disk, an optical disk, a magneto-optical disk, or a semiconductor memory. The removable recording medium 921 is, for example, a CD medium, a DVD medium, or a Blu-ray (registered trademark) medium. The removable recording medium 921 may be a Compact-Flash (CF; registered trademark), a flash memory, an SD memory card (Secure Digital Memory Card), or the like. Alternatively, the removable recording medium 921 may be, for example, an IC card (Integrated Circuit Card) equipped with a non-contact IC chip or an electronic device.

The connection port 917 is a port for allowing devices to directly connect to the arithmetic processing apparatus 200. Examples of the connection port 917 include a USB (Universal Serial Bus) port, an IEEE1394 port, a SCSI (Small Computer System Interface) port, an RS-232C port, and the like. By the externally connected apparatus 923 connecting to this connection port 917, the arithmetic processing apparatus 200 directly obtains various data from the externally connected apparatus 923 and provides various data to the externally connected apparatus 923.

The communication device 919 is a communication interface configured from, for example, a communication device for connecting to a communication network 925. The communication device 919 is, for example, a wired or wireless LAN (Local Area Network), Bluetooth (registered trademark), a communication card for WUSB (Wireless USB), or the like. Alternatively, the communication device 919 may be a router for optical communication, a router for ADSL (Asymmetric Digital Subscriber Line), a modem for various communications, or the like. This communication device 919 can transmit and receive signals and the like in accordance with a predetermined protocol such as TCP/IP on the Internet and with other communication devices, for example. The communication network 925 connected to the communication device 919 is configured from a network and the like, which is connected via wire or wirelessly, and may be, for example, the Internet, a home LAN, an office LAN, infrared communication, radio wave communication, satellite communication, or the like.

Heretofore, an example of the hardware configuration capable of realizing the functions of the arithmetic processing apparatus 200 according to an embodiment of the present invention has been shown. Each of the structural elements described above may be configured using a general-purpose material, or may be configured from hardware dedicated to the function of each structural element. Accordingly, the hardware configuration to be used can be changed as appropriate according to the technical level at the time of carrying out the present embodiment.

EXAMPLES

Now, the shape measurement apparatus and the shape measurement method according to the present invention will be described specifically with Examples. Here, Examples described below are merely examples of a shape measurement apparatus and a shape measurement method according to the present invention, and a shape measurement apparatus and a shape measurement method according to the present invention are not limited to Examples described below.

In Examples, an image of the surface of a steel sheet known to be flat was captured using the strip-shaped body image capturing apparatus 100 illustrated in FIG. 2.

On this occasion, a superluminescent diode capable of emitting light of a wavelength of 800 nm with a spectral half-width of 30 nm was used as the linear light source 101, and linear light was applied from a position 300 mm away from the steel sheet surface toward the steel sheet surface while being focused so as to satisfy angle of incidence θ=83 degrees. The wavelength λ and the angle of incidence θ of linear light described above satisfy the relationship expressed by Formula (3) above. Note that the line width LW of linear light on the steel sheet surface was set to 2 mm, and power density of linear light on the steel sheet surface was set to 55 mW/cm².

As the screen 103, an Al₂O₃ plate provided with an Al₂O₃ film on the surface was used. In regard to the screen 103, the mean width RSm of the roughness profile elements on the projection plane was 0.01 mm, and this RSm value satisfied the aforementioned condition.

As the area camera 105, an area camera equipped with a typical image sensor was used. A separation distance between the screen 103 and the area camera 105 (the distance L in FIG. 14) was set to 350 mm. An image capturing resolution on the projection plane of the screen 103 when this area camera 105 was used was 0.2 mm/pixel.

In addition, for comparison, a laser light source of a wavelength of 810 nm with a spectral half-width of 1 nm was used, and image capturing was performed with other conditions set to similar conditions.

In regard to two types of captured images obtained, a center position of a line width of a reflected image was calculated by center-of-gravity operation using luminance values, and shift of the center position was specified along the width direction of the screen.

Figure 18A:
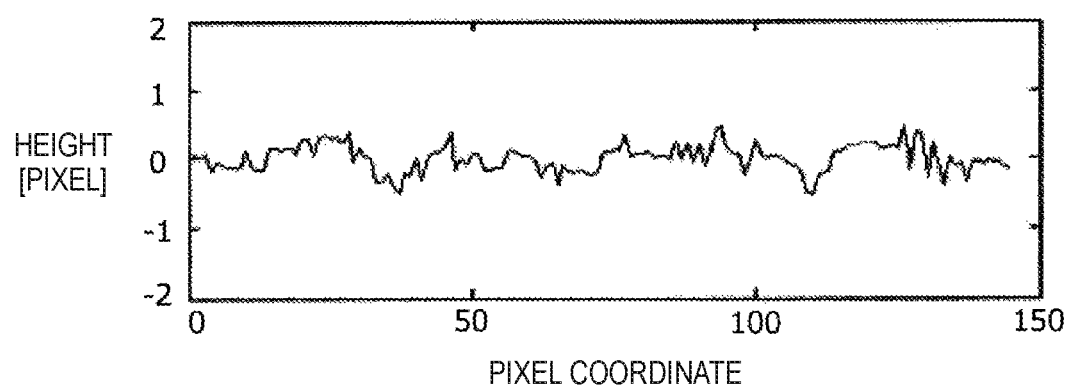
FIG. 18A is an explanatory diagram for Examples.
Figure 18B:
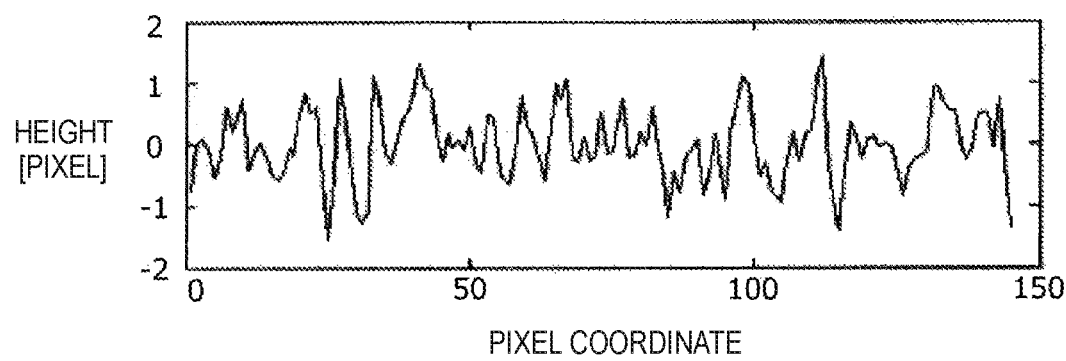
FIG. 18B is an explanatory diagram for Examples.

The obtained results are shown in FIGS. 18A and 18B. FIG. 18A shows the result when the superluminescent diode was used as the linear light source 101, and FIG. 18B shows the result when the laser light source was used as the linear light source 101. In FIGS. 18A and 18B, the units of the vertical axis and the horizontal axis are pixels, and one pixel corresponds to 0.2 mm.

In Examples, since an image of the surface of the steel sheet known to be flat was captured, shift of the center position of the line width of the reflected image is ideally expected to be substantially flat. It is apparent from comparison between FIGS. 18A and 18B that speckle noise occurred and the center position of the line width of the reflected image exhibited significant fluctuation in the case where the laser light source was used, whereas fluctuation of the center position of the line width of the reflected image was favorably suppressed in the case where the superluminescent diode was used. Standard deviation of height was calculated for both of FIGS. 18A and 18B; the standard deviation was 0.2 pixels (=0.04 mm) in FIG. 18A, whereas the standard deviation was 0.6 pixels (=0.12 mm) in FIG. 18B. That is, using the strip-shaped body image capturing apparatus 100 according to the present invention enabled a three-fold improvement in precision, as compared with an image capturing apparatus using a conventional laser light source.

The preferred embodiment(s) of the present invention has/have been described above with reference to the accompanying drawings, whilst the present invention is not limited to the above examples. A person skilled in the art may find various alterations and modifications within the scope of the appended claims, and it should be understood that they will naturally come under the technical scope of the present invention.

REFERENCE SIGNS LIST 10 shape measurement apparatus
100 strip-shaped body image capturing apparatus
101 linear light source
103 screen
105 area camera
200 arithmetic processing apparatus
201 image capturing control unit
203 data acquisition unit
205 image processing unit
207 display control unit
209 storage unit
221 inclination angle calculation unit
223 height calculation unit
225 result output unit

The invention claimed is:

1. A shape measurement apparatus configured to measure a surface shape of a strip-shaped body made of a metallic body, the shape measurement apparatus comprising:
a linear light source that includes a superluminescent diode and applies linear light spreading in a width direction of the strip-shaped body to a surface of the strip-shaped body;
a screen on which reflected light of the linear light off the surface of the strip-shaped body is projected;
an area camera that captures an image of the reflected light of the linear light projected on the screen; and
an arithmetic processing apparatus that calculates the surface shape of the strip-shaped body using the captured image of the reflected light of the linear light captured by the area camera,
wherein the linear light source has a spectral half-width of 20 nm or more, and is placed in a manner that an angle θ formed by an optical axis of the linear light source and a direction normal to the surface of the strip-shaped body and a wavelength λ of the linear light satisfy Formula (I) below related to specularity of the strip-shaped body, $$\frac{\cos\theta}{\lambda} \le \frac{1}{2\pi} \quad \text{Formula (I)}$$

wherein on the surface of the strip-shaped body, a line width W of the linear light along a longitudinal direction of the strip-shaped body is controlled so as to satisfy Formula (II) below, $$\frac{W}{L_{min}} \le \frac{\lambda}{2\pi} \quad \text{(Formula II)}$$

where $L_{min}$ is a minimum value of a size of the surface shape to be measured along the longitudinal direction, and λ is the wavelength of the linear light, and
wherein the linear light source is arranged so that the linear light is irradiated onto the surface of the strip-shaped body while wound around a roll having a predetermined curvature.

2. The shape measurement apparatus according to claim 1, wherein the wavelength of the linear light is equal to or greater than 800 nm and equal to or less than 1700 nm.

3. The shape measurement apparatus according to claim 1, wherein the linear light source is placed on the basis of the Formula (I) in a manner that the angle θ formed by the optical axis of the linear light source and the direction normal to the surface of the strip-shaped body falls within a range of equal to or greater than 74 degrees and equal to or less than 88 degrees.

4. The shape measurement apparatus according to claim 1, wherein power density of the linear light on the surface of the strip-shaped body is 55 mW/cm$^2$ or more.

5. The shape measurement apparatus according to claim 1, wherein in regard to surface roughness of a projection plane of the reflected light of the linear light on the screen, a mean width RSm of roughness profile elements prescribed in JIS B0601:2001 is 10 times or more greater than the wavelength of the linear light, and is 1/10 or less of a line width of the reflected light of the linear light along a height direction of the screen on the screen.

6. The shape measurement apparatus according to claim 1, wherein the arithmetic processing apparatus calculates an inclination angle of the surface of the strip-shaped body as information on the surface shape, on the basis of an amount of displacement of the reflected light from a reference position in the captured image.

7. The shape measurement apparatus according to claim 6, wherein the arithmetic processing apparatus calculates a height of the surface of the strip-shaped body as information on the surface shape, by integrating a tangent of the calculated inclination angle of the surface of the strip-shaped body along a relative movement direction of the area camera and the strip-shaped body.

8. The shape measurement apparatus according to claim 6, wherein the arithmetic processing apparatus inspects a shape of the strip-shaped body by comparing the calculated inclination angle of the surface of the strip-shaped body with a predetermined threshold value.

9. A shape measurement method configured to measure a surface shape of a strip-shaped body made of a metallic body, the shape measurement method comprising:
an irradiation step of applying linear light spreading in a width direction of the strip-shaped body to a surface of the strip-shaped body, using a linear light source that includes a superluminescent diode;
a step of projecting, on a screen, reflected light of the linear light off the surface of the strip-shaped body;
an image capturing step of capturing an image of the reflected light of the linear light projected on the screen, using an area camera; and
a calculation step of calculating the surface shape of the strip-shaped body using the captured image of the reflected light of the linear light captured by the area camera,
wherein the linear light source has a spectral half-width of 20 nm or more, and is placed in a manner that an angle θ formed by an optical axis of the linear light source and a direction normal to the surface of the strip-shaped body and a wavelength λ of the linear light satisfy Formula (I) below related to specularity of the strip-shaped body, $$\frac{\cos\theta}{\lambda} \leq \frac{1}{2\pi} \qquad \text{Formula (I)}$$

wherein on the surface of the strip-shaped body, a line width W of the linear light along a longitudinal direction of the strip-shaped body is controlled so as to satisfy Formula (II) below, $$\frac{W}{L_{min}} \leq \frac{\lambda}{2\pi} \qquad \text{(Formula II)}$$

where $L_{min}$ is a minimum value of a size of the surface shape to be measured along the longitudinal direction, and λ is the wavelength of the linear light, and
wherein the linear light source is arranged so that the linear light is irradiated onto the surface of the strip-shaped body while wound around a roll having a predetermined curvature.

10. The shape measurement method according to claim 9, wherein the wavelength of the linear light is equal to or greater than 800 nm and equal to or less than 1700 nm.

11. The shape measurement method according to claim 9, wherein the linear light source is placed on the basis of the Formula (I) in a manner that the angle θ formed by the optical axis of the linear light source and the direction normal to the surface of the strip-shaped body falls within a range of equal to or greater than 74 degrees and equal to or less than 88 degrees.

12. The shape measurement method according to claim 9, wherein power density of the linear light on the surface of the strip-shaped body is 55 mW/cm$^2$ or more.

13. The shape measurement method according to claim 9, wherein in regard to surface roughness of a projection plane of the reflected light of the linear light on the screen, a mean width RSm of roughness profile elements prescribed in JIS B0601:2001 is 10 times or more greater than the wavelength of the linear light, and is 1/10 or less of a line width of the reflected light of the linear light along a height direction of the screen on the screen.

14. The shape measurement method according to claim 9, wherein the calculation step calculates an inclination angle of the surface of the strip-shaped body as information on the surface shape, on the basis of an amount of displacement of the reflected light from a reference position in the captured image.

15. The shape measurement method according to claim 14, wherein the calculation step calculates a height of the surface of the strip-shaped body as information on the surface shape, by integrating a tangent of the calculated inclination angle of the surface of the strip-shaped body along a relative movement direction of the area camera and the strip-shaped body.

16. The shape measurement method according to claim 14, further comprising
an inspection step of inspecting a shape of the strip-shaped body by comparing the calculated inclination angle of the surface of the strip-shaped body with a predetermined threshold value.

* * * * *